(12) United States Patent
Jian et al.

(10) Patent No.: US 12,349,808 B2
(45) Date of Patent: Jul. 8, 2025

(54) ADJUSTABLE BED SYSTEM WITH MULTIPLE FUNCTIONS

(71) Applicant: Nisco Co., Ltd., Jiangsu (CN)

(72) Inventors: Sun Jian, Jiangsu (CN); Qiaoyan Yang, Jiangsu (CN); Wei Wang, Jiangsu (CN); Jian Xie, Jiangsu (CN); Yifan Mao, Jiangsu (CN)

(73) Assignee: NISCO CO., LTD, Jiangsu (CN)

( * ) Notice: Subject to any disclaimer, the term of this patent is extended or adjusted under 35 U.S.C. 154(b) by 392 days.

(21) Appl. No.: 17/950,297

(22) Filed: Sep. 22, 2022

(65) Prior Publication Data
US 2023/0021490 A1 Jan. 26, 2023

Related U.S. Application Data

(63) Continuation-in-part of application No. 16/990,085, filed on Aug. 11, 2020, now Pat. No. 11,602,228, and
(Continued)

(51) Int. Cl.
| | |
|---|---|
| *A47C 31/00* | (2006.01) |
| *A47C 20/04* | (2006.01) |
| *A47C 21/04* | (2006.01) |
| *A47C 27/05* | (2006.01) |
| *A47C 27/14* | (2006.01) |

(Continued)

(52) U.S. Cl.
CPC .............. *A47C 31/005* (2013.01); *A47C 20/04* (2013.01); *A47C 21/044* (2013.01); *A47C 27/056* (2013.01); *A47C 27/148* (2013.01); *A47C 27/15* (2013.01); *A61M 21/02* (2013.01); *A61M 2021/0016* (2013.01)

(58) Field of Classification Search
CPC ....... A47C 31/00; A47C 31/005; A47C 20/04; A61M 2021/0016
See application file for complete search history.

(56) References Cited

U.S. PATENT DOCUMENTS 5,175,791 A * 12/1992 Muderlak ................. A61L 9/03
   261/DIG. 89
5,645,578 A * 7/1997 Daffer ............... A61M 21/0094
   600/27
(Continued)

*Primary Examiner* — Fredrick C Conley
(74) *Attorney, Agent, or Firm* — troutman pepper locke; Tim Tingkang Xia, Esq.

(57) ABSTRACT

A bed system with multiple functions includes a frame structure; a plurality of platforms disposed on the frame structure; an adjustable assembly coupled with the frame structure and the plurality of platforms for operably adjusting one or more of the plurality of platforms in desired positions; a plurality of fans mounted onto openings in the plurality of platforms and adapted for operably providing air circulation in a surrounding space of the bed system, and an aromatherapy system attached onto the one or more platforms for producing desired fragrance in the surrounding space so as to promote health and well-being of a user. Each aromatherapy device is configured to produce a fragrance when said aromatherapy device is turned on, and one or more working modes. The fragrance is identical to or different from that produced by other aromatherapy device of the one or more aromatherapy devices.

10 Claims, 24 Drawing Sheets

Related U.S. Application Data a continuation-in-part of application No. 16/993,393, filed on Aug. 14, 2020, now abandoned, and a continuation-in-part of application No. 16/986,370, filed on Aug. 6, 2020, now abandoned, which is a continuation-in-part of application No. 16/732,826, filed on Jan. 2, 2020, now abandoned.

(60) Provisional application No. 62/889,145, filed on Aug. 20, 2019, provisional application No. 62/889,112, filed on Aug. 20, 2019, provisional application No. 62/889,127, filed on Aug. 20, 2019, provisional application No. 62/790,583, filed on Jan. 10, 2019.

(51) Int. Cl.
*A47C 27/15* (2006.01)
*A61M 21/02* (2006.01)
*A61M 21/00* (2006.01)

(56) References Cited

U.S. PATENT DOCUMENTS

| | | | |
|---|---|---|---|
| 9,918,556 B2 * | 3/2018 | Rawls-Meehan | A47C 27/082 |
| 2004/0265164 A1 * | 12/2004 | Woo | B60H 3/0035 |
| | | | 422/4 |
| 2008/0148481 A1 * | 6/2008 | Brykalski | A47C 21/048 |
| | | | 5/423 |
| 2010/0011502 A1 * | 1/2010 | Brykalski | A61G 7/05 |
| | | | 5/423 |
| 2015/0335162 A1 * | 11/2015 | Rawls-Meehan | |
| | | | A61G 7/05769 |
| | | | 5/617 |
| 2016/0022518 A1 * | 1/2016 | Shih | A61G 7/015 |
| | | | 5/616 |
| 2017/0173203 A1 * | 6/2017 | Becker | A61L 9/12 |

* cited by examiner

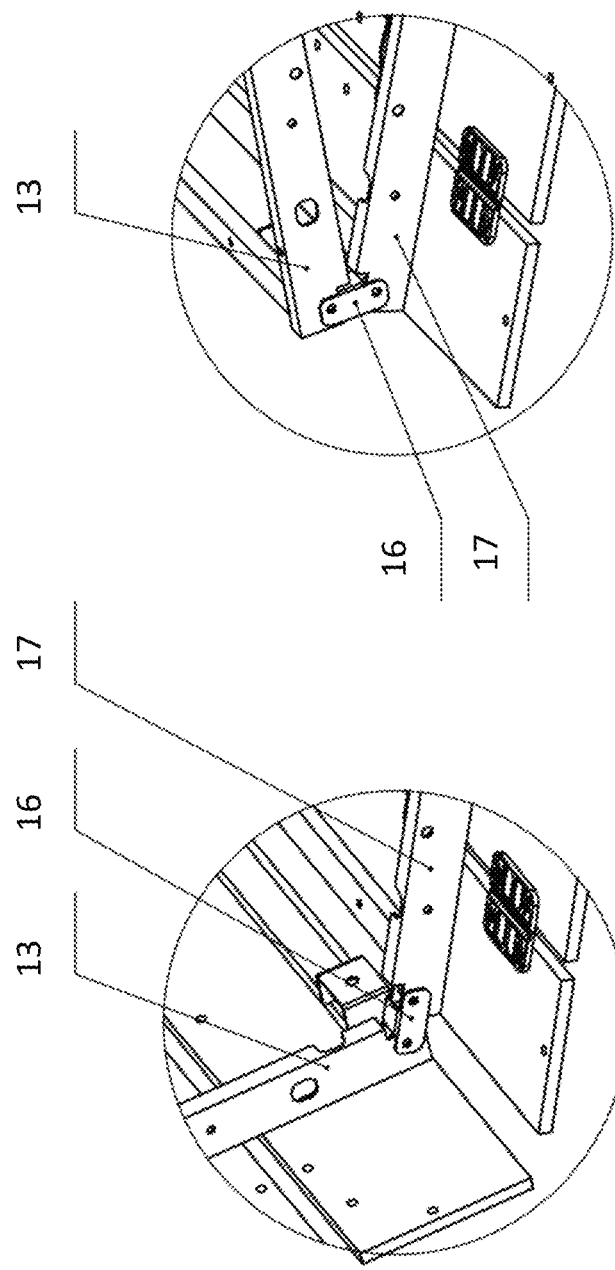

ADJUSTABLE BED SYSTEM WITH MULTIPLE FUNCTIONS

CROSS-REFERENCE TO RELATED PATENT APPLICATIONS

This application is a continuation-in-part application of U.S. patent application Ser. No. 16/990,085, filed Aug. 11, 2020, which itself claims priority to and the benefit of U.S. Provisional Patent Application Ser. Nos. 62/889,145, filed Aug. 20, 2019.

This application is also a continuation-in-part application of U.S. patent application Ser. No. 16/993,393, filed Aug. 14, 2020, which itself claims priority to and the benefit of U.S. Provisional Patent Application Ser. No. 62/889,112, filed Aug. 20, 2019.

This application is also a continuation-in-part application of U.S. patent application Ser. No. 16/986,370, filed Aug. 6, 2020, which itself claims priority to and the benefit of U.S. Provisional Patent Application Ser. No. 62/889,127, filed Aug. 20, 2019, and is also a continuation-in-part application of U.S. patent application Ser. No. 16/732,826, filed Jan. 2, 2020, which itself claims priority to and the benefit of U.S. Provisional Patent Application Ser. No. 62/790,583, filed Jan. 10, 2019.

Each of the above identified applications is incorporated herein in its entirety by reference.

FIELD OF THE INVENTION

The invention generally relates to a bed, and more particular to an adjustable bed with multiple functions.

BACKGROUND OF THE INVENTION

Sleep is critical for people in every aspect of their lives. Beds are necessary furniture for people to sleep on. Thus, it is beneficial and desirable for people to have a bed system that is capable of adjusting body positions based on user's sleep preference so that the user achieves maximum comfort during sleeping. In addition, it is also beneficial and desirable that the bed system has therapeutic functions to promote health and well-being of a user.

SUMMARY OF THE INVENTION

The invention, in one aspect, relates to a mattress for a bed system. The mattress comprises a plurality of layers vertically stacked to one another, the plurality of layers comprising at least a first layer, a second layer and a third layer, wherein the first layer comprises a plurality of openings defined therein being operably in fluidic communication with a plurality of fans for providing air circulation to a user through the mattress, wherein each opening in the first layer is operably aligned with and is in fluidic commination with a respective one of the plurality of fans, and wherein the second layer is disposed between the first layer and the third layer and comprises an array of springs.

In one embodiment, the first layer is formed of a flex support foam for providing corner to corner support, and wherein the third layer of formed of a flex comfort foam.

In one embodiment, the array of springs comprises pocket springs and/or hybrid support-springs for providing ventilation and thorough foundation.

In one embodiment, the second layer further comprises four side walls defining a housing therewith for accommodating the array of springs.

In one embodiment, the plurality of layers further comprises a fourth layer disposed on the third layer, and a fifth layer disposed on the fourth layer, wherein the fourth layer is formed of a ventilated bamboo charcoal memory foam, wherein the ventilated bamboo charcoal memory foam comprises a memory foam infused with bamboo charcoal, for regulating moisture, odor and/or temperature, and wherein the fifth layer is formed of a smart foam that is breathable, flexible and operably adapts to body natural contours of the user.

The mattress further comprises an aromatherapy system attached onto one or more of the plurality of layers for producing desired fragrance in a surrounding space of the bed system so as to promote health and well-being of a user.

In one embodiment, the aromatherapy system is an electric aromatherapy system comprising one or more aromatherapy devices, wherein each aromatherapy device is configured to produce a fragrance when said aromatherapy device is turned on, wherein the fragrance is identical to or different from that produced by other aromatherapy device of the one or more aromatherapy devices.

In one embodiment, each aromatherapy device has one or more working modes, wherein the one or more working modes comprises a first working mode in which said aromatherapy device is turned on or turned off based on the user's instruction; a second working mode in which said aromatherapy device is turned on for a first period of time, and then turned off; and a third working mode in which said aromatherapy device is turned on for a second period of time regularly in a third period of time.

In one embodiment, each aromatherapy device comprises a container for containing an aromatic substance; a diffuser coupled to the container for operably heating the aromatic substance therein so as to produce the fragrance; and one or more indicators, each indicator for indicating one of the one or more working modes of said aromatherapy device.

In one embodiment, each aromatherapy device is controllable to operate in one of the one or more working modes by a remote control or an APP installed in a smart electronic device.

In addition, the mattress also comprises one or more sensors attached on one of plurality of layers for measuring environment parameters of the surrounding space, and/or physiological parameters of the user during sleeping, wherein the environment parameters of the surrounding space include moisture, odor and/or temperature, and the physiological parameters of the user include a body temperature, a heart rate, and/or a respiratory rate.

In one embodiment, the one or more sensors comprise at least one of moisture sensors, odor sensors, temperature sensors, heart rate sensors, and respiratory rate sensors.

In one embodiment, the one or more sensors is in wired or wireless communications with a controller that is configured to receive the measured environment parameters and/or the monitored physiological parameters from the one or more sensors, process them therein, and wirelessly transmit the processed environment parameters and/or the processed physiological parameters to a database and/or a smart electronic device.

In another aspect, the invention relates to a bed system with multiple functions. The bed system comprises a frame structure; a plurality of platforms disposed on the frame structure; an adjustable assembly coupled with the frame structure and the plurality of platforms for operably adjusting one or more of the plurality of platforms in desired positions; a plurality of fans mounted onto openings in the plurality of platforms and adapted for operably providing air circulation in a surrounding space of the bed system; and an aromatherapy system attached onto one or more of the plurality of platforms for producing desired fragrance in the surrounding space so as to promote health and well-being of a user.

In one embodiment, the aromatherapy system is an electric aromatherapy system comprising one or more aromatherapy devices, wherein each aromatherapy device is configured to produce a fragrance when said aromatherapy device is turned on, wherein the fragrance is identical to or different from that produced by other aromatherapy device of the one or more aromatherapy devices.

In one embodiment, each aromatherapy device has one or more working modes, wherein the one or more working modes comprises a first working mode in which said aromatherapy device is turned on or turned off based on the user's instruction; a second working mode in which said aromatherapy device is turned on for a first period of time, and then turned off; and a third working mode in which said aromatherapy device is turned on for a second period of time regularly in a third period of time.

In one embodiment, each aromatherapy device is controllable to operate in one of the one or more working modes by a remote control and/or an APP installed in a smart electronic device.

In one embodiment, the bed system further comprises a mattress comprising a plurality of layers vertically stacked to one another, the plurality of layers comprising at least a first layer having a plurality of openings defined therein and being operably in fluidic communication with the plurality of fans for providing air circulation to a user through the mattress, wherein the mattress is placed on the plurality of platforms such that each opening in the first layer of the mattress is directly aligned with and is in fluidic commination with a respective one of the plurality of fans.

In one embodiment, the mattress further comprises one or more sensors attached on one of plurality of layers for measuring environment parameters of the surrounding space, and/or physiological parameters of the user during sleeping, wherein the environment parameters of the surrounding space include moisture, odor and/or temperature, and the physiological parameters of the user include a body temperature, a heart rate, and/or a respiratory rate.

In one embodiment, the one or more sensors is in wired or wireless communications with a controller that is configured to receive the measured environment parameters and/or the monitored physiological parameters from the one or more sensors, process them therein, and wirelessly transmit the processed environment parameters and/or the processed physiological parameters to a database and/or a smart electronic device.

In one embodiment, the controller is further configured to individually or cooperatively control operations of the adjustable assembly, the plurality of fans, and the aromatherapy system, by operation instruction received from a remote control and/or an APP installed in a smart electronic device.

In one embodiment, the adjustable assembly comprises a back lifting assembly comprising a back lifting bracket pivotally connected to the frame structure, and a back lifting actuator pivotally connected between the back lifting bracket and the frame structure for operably driving the back lifting bracket to pivotally move in an upward rotating direction or a downward rotating direction relative to the frame structure; and a leg lifting assembly comprising a leg lifting bracket pivotally connected to the frame structure, and a leg lifting actuator pivotally connected between the leg lifting bracket and the frame structure for operably driving the leg lifting bracket to pivotally move in an upward rotating direction or a downward rotating direction relative to the frame structure.

In one embodiment, the back lifting bracket comprises a middle bar and a pair of swing arms, wherein the pair of swing arms is transversely spaced and longitudinally extended, and rigidly connected to ends of the transversely extending middle bar, and each of the pair of swing arms has a first end portion and an opposite, second end portion, wherein the first end portion of each swing arm is pivotally mounted to the frame structure. The back lifting actuator comprises a motor member, an outer tube extending from the motor member, an activation rod received in the outer tube, engaged with the motor member and configured to be telescopically movable relative to said outer tube according to a direction of motor rotation, wherein the motor member is pivotally connected to the frame structure, and the activation rod has a distal end portion pivotally connected to the middle bar of the back lifting bracket, or wherein the motor member is pivotally connected to the middle bar of the back lifting bracket, and the activation rod has a distal end portion pivotally connected to the frame structure.

In one embodiment, the leg lifting bracket comprises a middle bar and a pair of swing arms, wherein the pair of swing arms is transversely spaced and longitudinally extended, and rigidly connected to ends of the transversely extending middle bar, and each of the pair of swing arms has a first end portion and an opposite, second end portion, wherein the first end portion of each swing arm is pivotally mounted to the frame structure. The leg lifting actuator comprises a motor member, an outer tube extending from the motor member, an activation rod received in the outer tube, engaged with the motor member and configured to be telescopically movable relative to said outer tube according to a direction of motor rotation, wherein the motor member is pivotally connected to the frame structure, and the activation rod has a distal end portion pivotally connected to the middle bar of the leg lifting bracket, or wherein the motor member is pivotally connected to the middle bar of the leg lifting bracket, and the activation rod has a distal end portion pivotally connected to the frame structure.

These and other aspects of the invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

FIGS. 10-11 shows schematically and partially two folding states of the frame structure shown in FIG. 8 in a folding state.

DETAILED DESCRIPTION OF THE INVENTION

Figure 1:
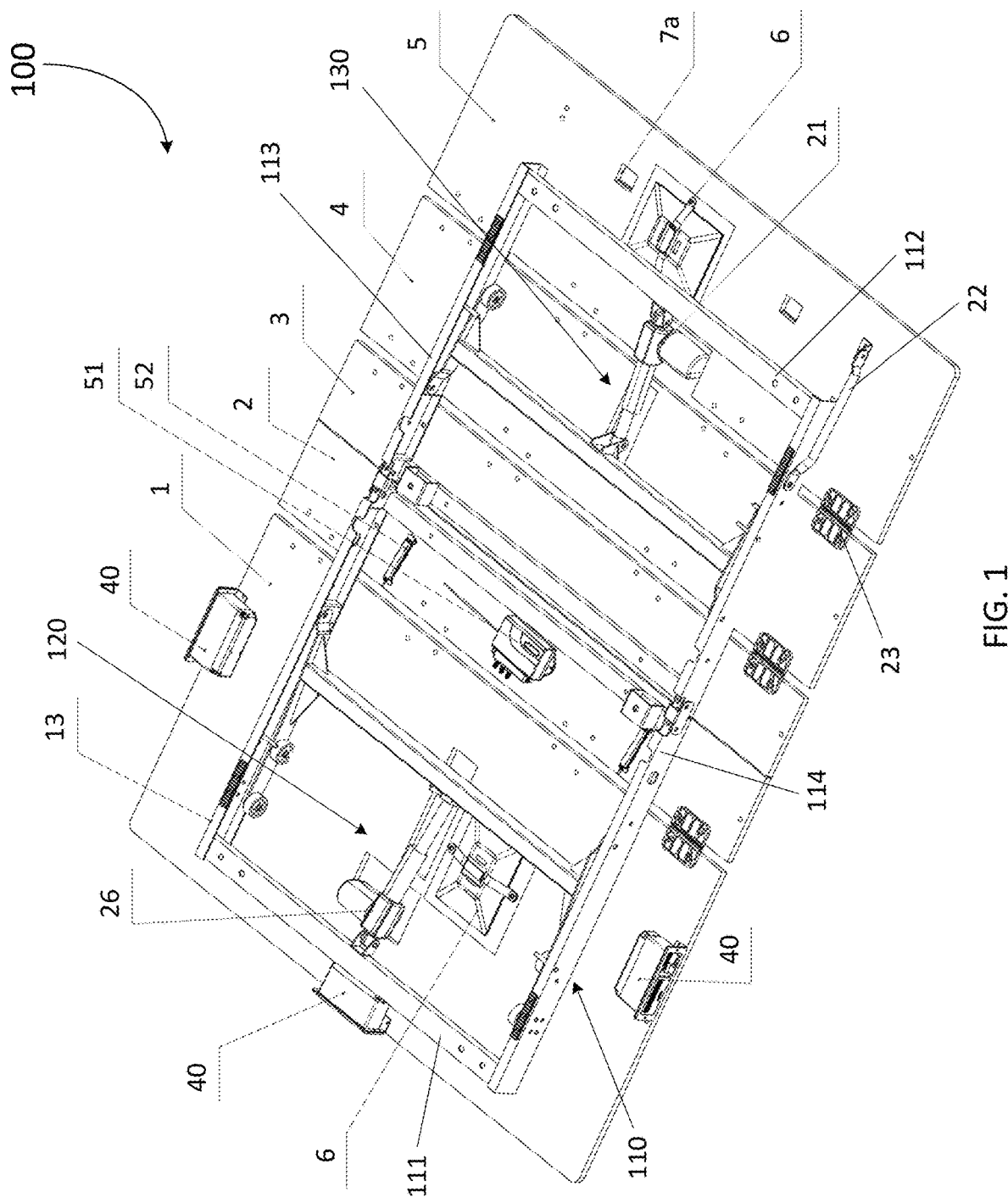
FIG. 1 shows schematically a rear perspective view of an adjustable bed according to one embodiment of the invention.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

As used herein, "around", "about", "substantially" or "approximately" shall generally mean within 20 percent, preferably within 10 percent, and more preferably within 5 percent of a given value or range. Numerical quantities given herein are approximate, meaning that the term "around", "about" "substantially" or "approximately" can be inferred if not expressly stated.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. In accordance with the purposes of this invention, as embodied and broadly described herein, this invention, in one aspect, relates to an adjustable bed system with an aromatherapy system, a power fan system, and/or a mattress with breathable and ventilation functions.

In one aspect of the invention, a mattress comprises a plurality of layers vertically stacked to one another, the plurality of layers comprising at least a first layer, a second layer and a third layer, wherein the first layer comprises a plurality of openings defined therein being operably in fluidic communication with a plurality of fans for providing air circulation to a user through the mattress, wherein each opening in the first layer is operably aligned with and is in fluidic commination with a respective one of the plurality of fans, and wherein the second layer is disposed between the first layer and the third layer and comprises an array of springs.

In one embodiment, the first layer is formed of a flex support foam for providing corner to corner support, and wherein the third layer of formed of a flex comfort foam.

In one embodiment, the array of springs comprises pocket springs and/or hybrid support-springs for providing ventilation and thorough foundation.

In one embodiment, the second layer further comprises four side walls defining a housing therewith for accommodating the array of springs.

In one embodiment, the plurality of layers further comprises a fourth layer disposed on the third layer, and a fifth layer disposed on the fourth layer, wherein the fourth layer is formed of a ventilated bamboo charcoal memory foam, wherein the ventilated bamboo charcoal memory foam comprises a memory foam infused with bamboo charcoal, for regulating moisture, odor and/or temperature, and wherein the fifth layer is formed of a smart foam that is breathable, flexible and operably adapts to body natural contours of the user.

The mattress further comprises an aromatherapy system attached onto one or more of the plurality of layers for producing desired fragrance in a surrounding space of the bed system so as to promote health and well-being of a user.

In one embodiment, the aromatherapy system is an electric aromatherapy system comprising one or more aromatherapy devices, wherein each aromatherapy device is configured to produce a fragrance when said aromatherapy device is turned on, wherein the fragrance is identical to or different from that produced by other aromatherapy device of the one or more aromatherapy devices.

In one embodiment, each aromatherapy device has one or more working modes, wherein the one or more working modes comprises a first working mode in which said aromatherapy device is turned on or turned off based on the user's instruction; a second working mode in which said aromatherapy device is turned on for a first period of time, and then turned off; and a third working mode in which said aromatherapy device is turned on for a second period of time regularly in a third period of time.

In one embodiment, each aromatherapy device comprises a container for containing an aromatic substance; a diffuser coupled to the container for operably heating the aromatic substance therein so as to produce the fragrance; and one or more indicators, each indicator for indicating one of the one or more working modes of said aromatherapy device.

In one embodiment, each aromatherapy device is controllable to operate in one of the one or more working modes by a remote control or an APP installed in a smart electronic device.

In addition, the mattress also comprises one or more sensors attached on one of plurality of layers for measuring environment parameters of the surrounding space, and/or physiological parameters of the user during sleeping, wherein the environment parameters of the surrounding space include moisture, odor and/or temperature, and the physiological parameters of the user include a body temperature, a heart rate, and/or a respiratory rate.

In one embodiment, the one or more sensors comprise at least one of moisture sensors, odor sensors, temperature sensors, heart rate sensors, and respiratory rate sensors.

In one embodiment, the one or more sensors is in wired or wireless communications with a controller that is configured to receive the measured environment parameters and/or the monitored physiological parameters from the one or more sensors, process them therein, and wirelessly transmit the processed environment parameters and/or the processed physiological parameters to a database and/or a smart electronic device.

In another aspect, the invention relates to a bed system with multiple functions. The bed system comprises a frame structure; a plurality of platforms disposed on the frame structure; an adjustable assembly coupled with the frame structure and the plurality of platforms for operably adjusting one or more of the plurality of platforms in desired positions; a plurality of fans mounted onto openings in the plurality of platforms and adapted for operably providing air circulation in a surrounding space of the bed system; and an aromatherapy system attached onto one or more of the plurality of platforms for producing desired fragrance in the surrounding space so as to promote health and well-being of a user.

In one embodiment, the aromatherapy system is an electric aromatherapy system comprising one or more aromatherapy devices, wherein each aromatherapy device is configured to produce a fragrance when said aromatherapy device is turned on, wherein the fragrance is identical to or different from that produced by other aromatherapy device of the one or more aromatherapy devices.

In one embodiment, each aromatherapy device has one or more working modes, wherein the one or more working modes comprises a first working mode in which said aromatherapy device is turned on or turned off based on the user's instruction; a second working mode in which said aromatherapy device is turned on for a first period of time, and then turned off; and a third working mode in which said aromatherapy device is turned on for a second period of time regularly in a third period of time.

In one embodiment, each aromatherapy device is controllable to operate in one of the one or more working modes by a remote control and/or an APP installed in a smart electronic device.

In one embodiment, the bed system further comprises a mattress comprising a plurality of layers vertically stacked to one another, the plurality of layers comprising at least a first layer having a plurality of openings defined therein and being operably in fluidic communication with the plurality of fans for providing air circulation to a user through the mattress, wherein the mattress is placed on the plurality of platforms such that each opening in the first layer of the mattress is directly aligned with and is in fluidic commination with a respective one of the plurality of fans.

In one embodiment, the mattress further comprises one or more sensors attached on one of plurality of layers for measuring environment parameters of the surrounding space, and/or physiological parameters of the user during sleeping, wherein the environment parameters of the surrounding space include moisture, odor and/or temperature, and the physiological parameters of the user include a body temperature, a heart rate, and/or a respiratory rate.

In one embodiment, the one or more sensors is in wired or wireless communications with a controller that is configured to receive the measured environment parameters and/or the monitored physiological parameters from the one or more sensors, process them therein, and wirelessly transmit the processed environment parameters and/or the processed physiological parameters to a database and/or a smart electronic device.

In one embodiment, the controller is further configured to individually or cooperatively control operations of the adjustable assembly, the plurality of fans, and the aromatherapy system, by operation instruction received from a remote control and/or an APP installed in a smart electronic device.

In one embodiment, the adjustable assembly comprises a back lifting assembly comprising a back lifting bracket pivotally connected to the frame structure, and a back lifting actuator pivotally connected between the back lifting bracket and the frame structure for operably driving the back lifting bracket to pivotally move in an upward rotating direction or a downward rotating direction relative to the frame structure; and a leg lifting assembly comprising a leg lifting bracket pivotally connected to the frame structure, and a leg lifting actuator pivotally connected between the leg lifting bracket and the frame structure for operably driving the leg lifting bracket to pivotally move in an upward rotating direction or a downward rotating direction relative to the frame structure.

In one embodiment, the back lifting bracket comprises a middle bar and a pair of swing arms, wherein the pair of swing arms is transversely spaced and longitudinally extended, and rigidly connected to ends of the transversely extending middle bar, and each of the pair of swing arms has a first end portion and an opposite, second end portion, wherein the first end portion of each swing arm is pivotally mounted to the frame structure. The back lifting actuator comprises a motor member, an outer tube extending from the motor member, an activation rod received in the outer tube, engaged with the motor member and configured to be telescopically movable relative to said outer tube according to a direction of motor rotation, wherein the motor member is pivotally connected to the frame structure, and the activation rod has a distal end portion pivotally connected to the middle bar of the back lifting bracket, or wherein the motor member is pivotally connected to the middle bar of the back lifting bracket, and the activation rod has a distal end portion pivotally connected to the frame structure.

In one embodiment, the leg lifting bracket comprises a middle bar and a pair of swing arms, wherein the pair of swing arms is transversely spaced and longitudinally extended, and rigidly connected to ends of the transversely extending middle bar, and each of the pair of swing arms has a first end portion and an opposite, second end portion, wherein the first end portion of each swing arm is pivotally mounted to the frame structure. The leg lifting actuator comprises a motor member, an outer tube extending from the motor member, an activation rod received in the outer tube, engaged with the motor member and configured to be telescopically movable relative to said outer tube according to a direction of motor rotation, wherein the motor member is pivotally connected to the frame structure, and the activation rod has a distal end portion pivotally connected to the middle bar of the leg lifting bracket, or wherein the motor member is pivotally connected to the middle bar of the leg lifting bracket, and the activation rod has a distal end portion pivotally connected to the frame structure.

Exemplary embodiments of the invention are described below in details in conjunction with the accompanying drawings in FIGS. 1-29. For purposes of clarity, the same reference numbers will be used in the drawings to identify similar elements. It should be understood that one or more steps within a method may be executed in different order (or concurrently) without altering the principles of the invention.

Referring to FIG. 1, the adjustable bed system 100 includes a frame structure 110, a plurality of platforms 1-5 disposed on the frame structure 110 and an adjustable assembly 120 and 130 coupled with the frame structure 110 and the plurality of platforms 1-5 for operably adjusting one or more of the plurality of platforms 1-5 in desired positions; and an aromatherapy system 40 attached onto the one or more platforms 1-5 for producing desired fragrance in a surrounding space of the adjustable bed 100 so as to promote health and well-being of a user. The term "platform" used herein refers to a bed board or board.

Figure 3:
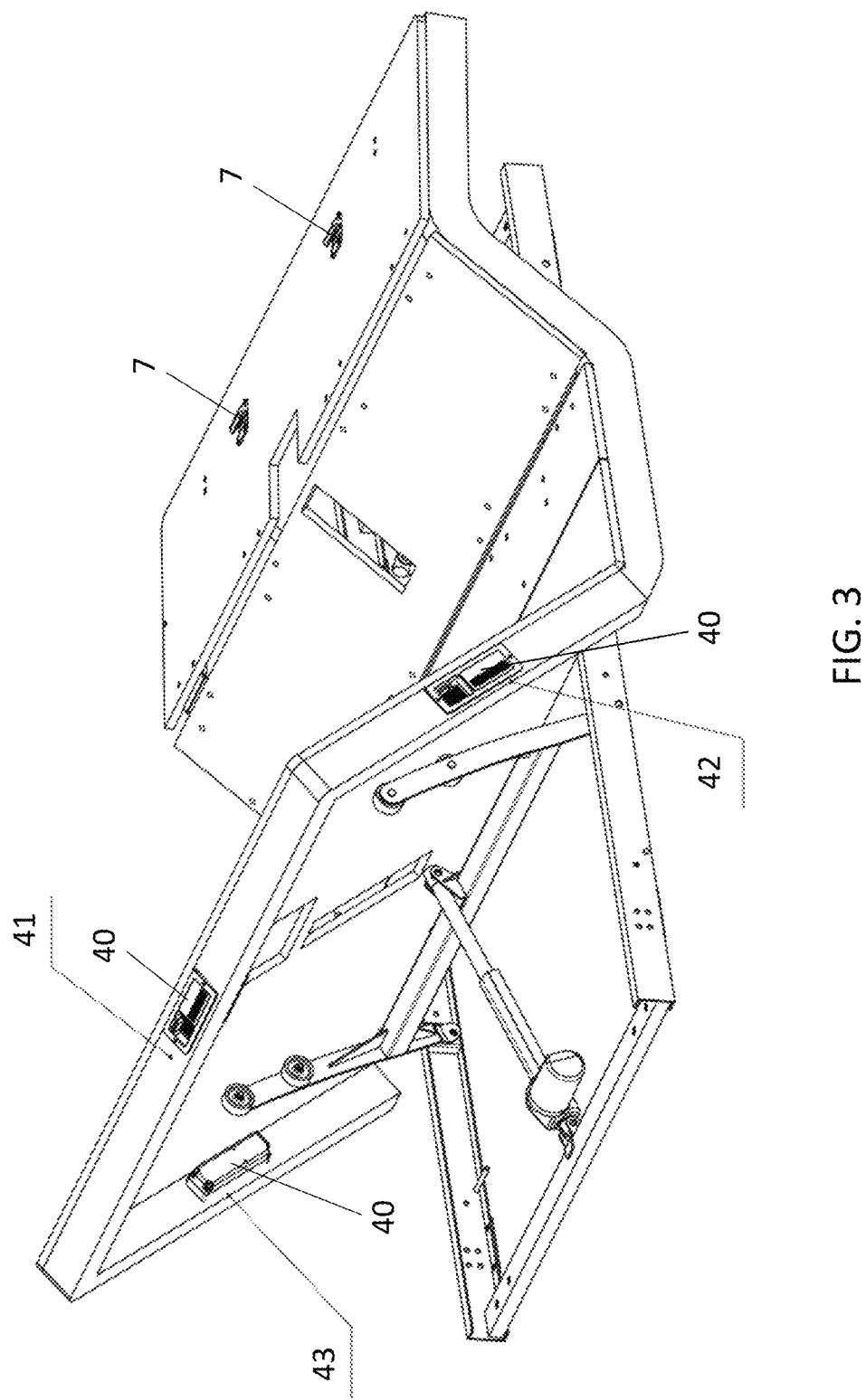
FIG. 3 shows schematically a front perspective view of an adjustable bed according to one embodiment of the invention.
Figure 4:
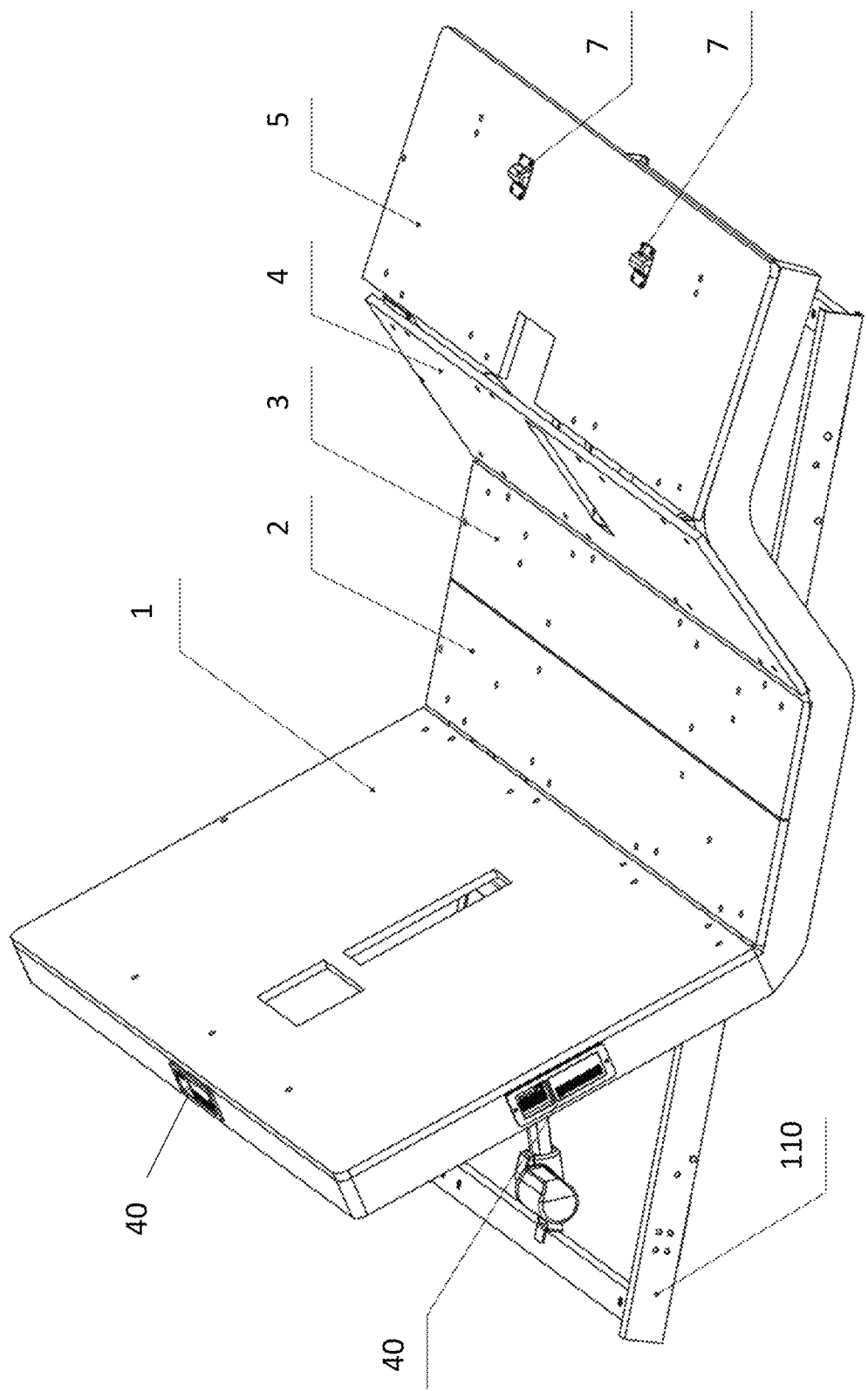
FIG. 4 shows schematically another front perspective view of the adjustable bed shown in FIG. 3.

In some embodiments, the aromatherapy system is an electric aromatherapy system comprising one or more aromatherapy devices 40. For example, as shown in FIG. 1, three aromatherapy devices 40 are employed and attached onto the back platform 1. It should be noted that other number of the aromatherapy devices 40 can also be utilized to practice the invention. In addition, the aromatherapy devices 40 can also be attached onto other platforms, or the frame structure 110. In addition, as shown in FIGS. 3-4, the edges of the plurality of platforms 1-5 are provided with side boards 41-42 for better appearance.

In some embodiments, each aromatherapy device is configured to produce a fragrance when said aromatherapy device is turned on. The fragrance is identical to or different from that produced by other aromatherapy device of the one or more aromatherapy devices.

In some embodiments, each aromatherapy device has one or more working modes. The one or more working modes comprises a first working mode in which said aromatherapy device is turned on or turned off based on the user's instruction; a second working mode in which said aromatherapy device is turned on for a first period of time (e.g., 1 minute), and then turned off; and a third working mode in which said aromatherapy device is turned on for a second period of time (e.g., 1 minute) regularly in each and every third period of time (e.g., each and every 2 hours).

In some embodiments, each aromatherapy device 40 can be individually or cooperatively controlled to operate in one of the one or more working modes by a remote control or an APP.

Figure 5:
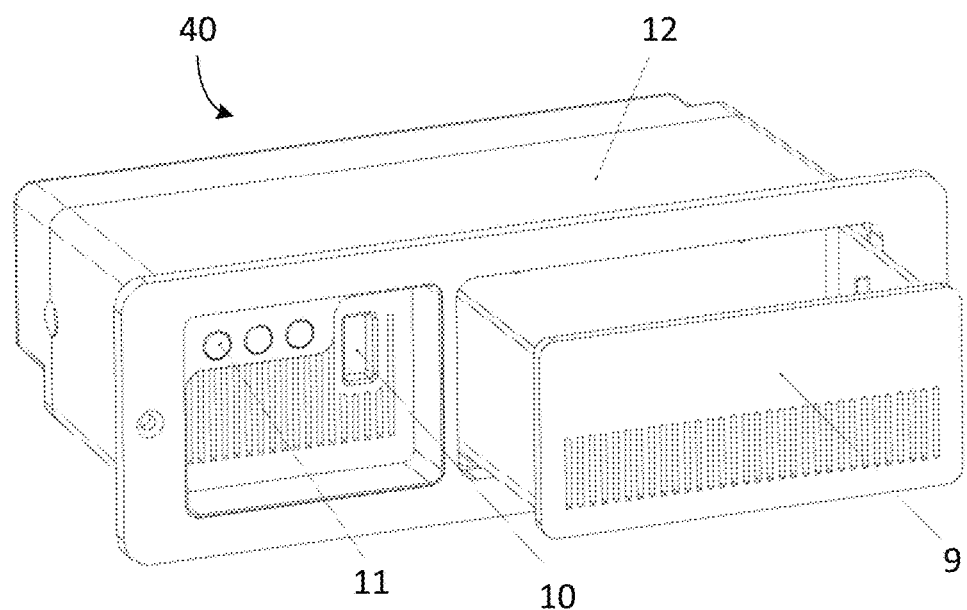
FIG. 5 shows schematically a front perspective view of an aromatherapy device according to one embodiment of the invention.

In one embodiment shown in FIG. 5, each aromatherapy device 40 comprises a container 9 for containing an aromatic substance; a diffuser coupled to the container 9 for operably heating the aromatic substance therein so as to produce the fragrance; and one or more indicators 11 with each indicator for indicating one of the one or more working modes of said aromatherapy device 40. Each aromatherapy device 40 also comprises a housing 12 for accommodating the container 9 and the indicators 11. The container 9 is detachable from the housing 12. In addition, each aromatherapy device 40 includes one or more USB port 10. According to the invention, each aromatherapy device 40 can contain an aromatic substance that is identical to or different from that of the aromatherapy devices 40.

The aromatic substance can be a substance extracted natural plants such as aromatic essential oils, or a chemically synthesized material. It is proven that aromatherapy using aromatic essential oils medicinally improves the health of the body, mind, and spirit, and has benefits including, but is not limited to, managing pain, improving sleep quality, reducing stress, agitation, and anxiety, soothing sore joints, treating headaches and migraines, and boosting immunity.

The capability of producing different fragrances from the one or more aromatherapy devices 40 and the controllability of the one or more aromatherapy devices 40 have particular therapeutic benefits for the user. For example, during wake up time, one aromatherapy devices 40 can be configured to produce a fresh air fragrance, while during a sleep time, the other aromatherapy devices 40 can be configured to produce a fragrance improving sleep quality of the user.

Figure 8:
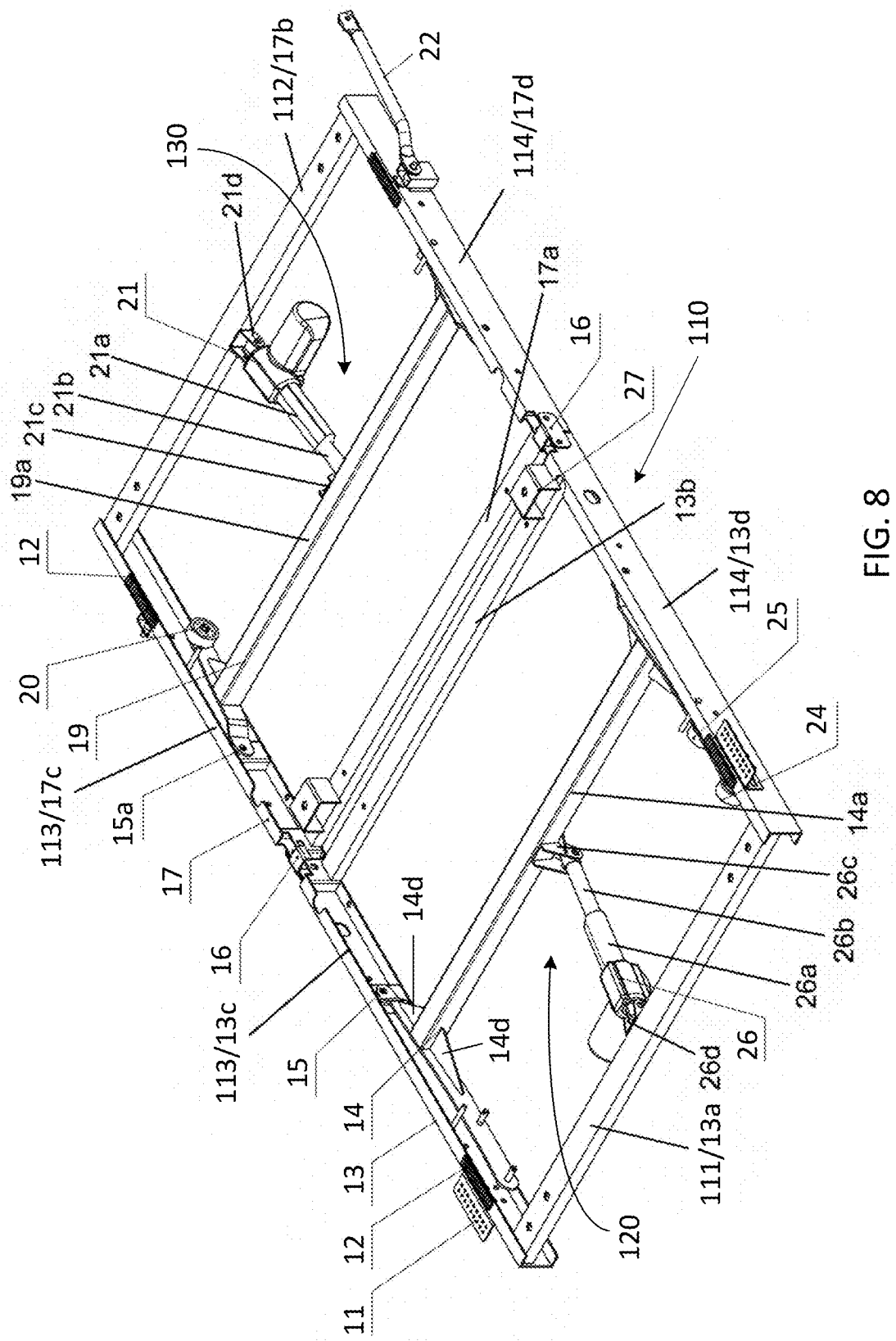
FIG. 8 shows schematically a front perspective view of a frame structure of the adjustable bed shown in FIG. 1 in a flat state.
Figure 9:
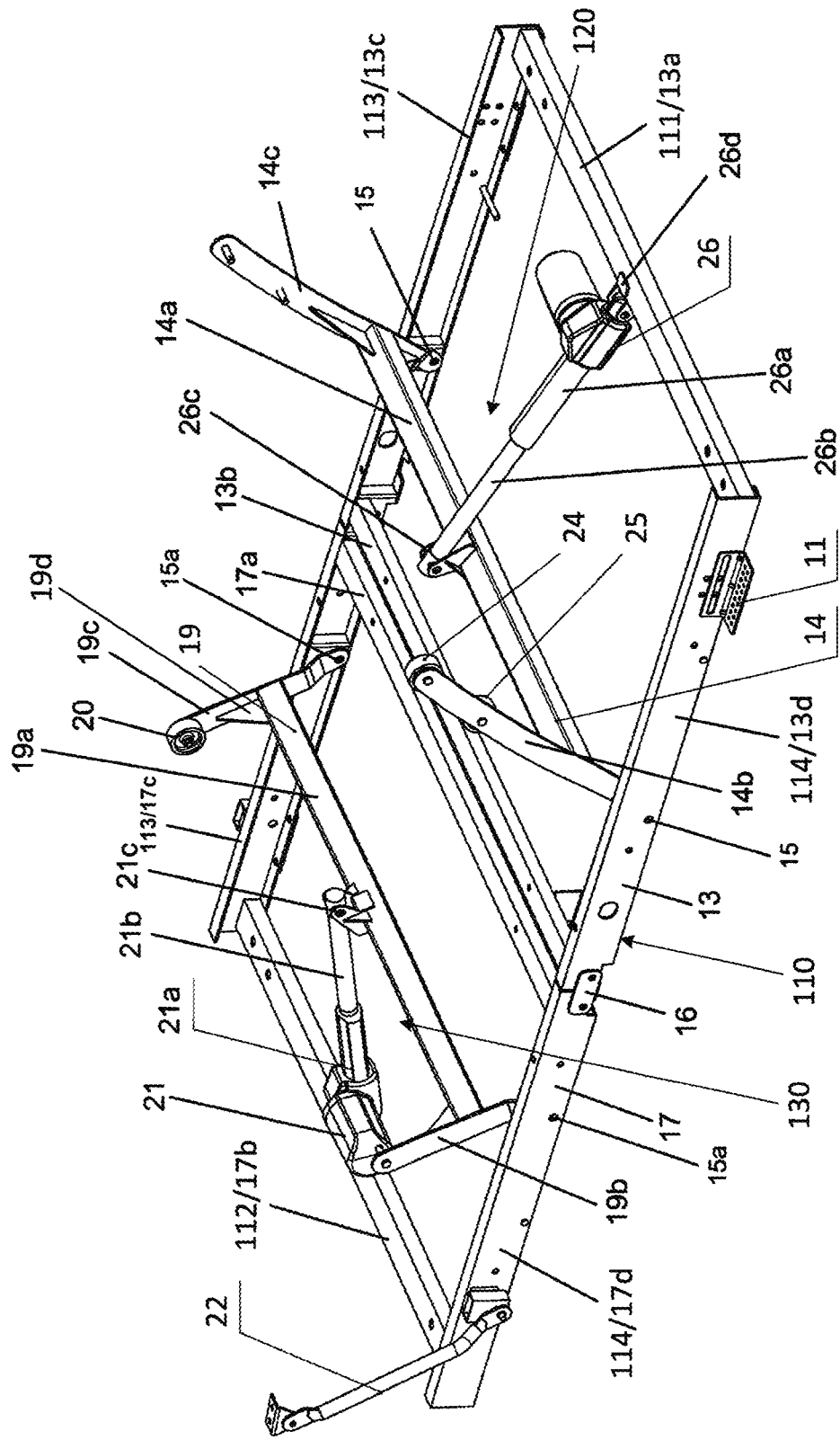
FIG. 9 shows schematically a front perspective view of the frame structure shown in FIG. 8 in an adjusting state.
Figure 12:
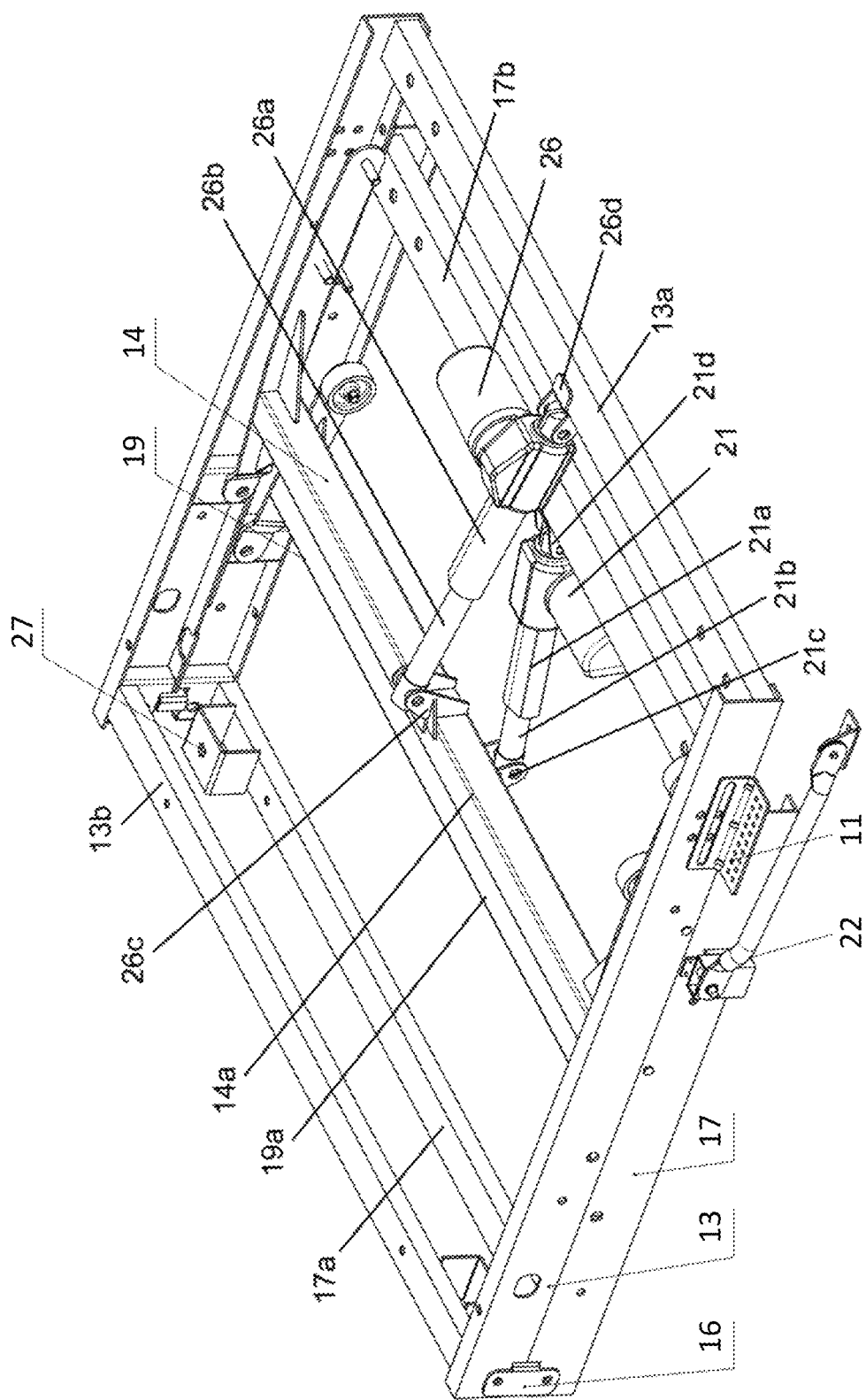
FIG. 12 shows schematically a front perspective view of the frame structure shown in FIG. 8 in a folding state.

In one embodiment, as shown FIGS. 1 and 8-9, the frame structure 110 includes an upper rail 111, a lower rail 112, and a pair of side rails 113 and 114. The upper rail 111 and the lower rail 112 are longitudinally spaced and transversely extended, and the pair of side rails 113 and 114 is transversely spaced and longitudinally extended, and rigidly connected to the upper rail 111 and the lower rail 112, such that the upper rail 111 and the lower rail 112 and the pair of side rails 113 and 114 are co-planar in a rectangle form. Preferably, the connection of the pair of side rails 113 and 114 to the upper and lower rails 111 and 112 is by welding ends of the upper rail 111 onto end portions of the pair of side rails 113 and 114, and welding ends of the lower rail 112 onto opposite end portions of the pair of side rails 113 and 114. Other connecting means can also be utilized to practice the invention.

The adjustable assembly includes a back lifting assembly 120 and a leg lifting assembly 130.

The back lifting assembly 120 has a back lifting bracket 14 pivotally connected to the side rails 113 and 114 of the frame structure 110, and a back lifting actuator 26 pivotally connected between the back lifting bracket 14 and the upper rail 111 of the frame structure 110 for operably driving the back lifting bracket 14 to pivotally move in an upward rotating direction or a downward rotating direction relative to the frame structure 110.

The back lifting bracket 14 includes a middle bar 14a and a pair of swing arms 14b and 14c. Each of the pair of swing arms 14b and 14c is in an arc-shaped design. The pair of swing arms 14b and 14c is transversely spaced and longitudinally extended, and rigidly connected to ends of the transversely extending middle bar 14a in an H-shaped form. Each of the pair of swing arms 14b and 14c has a first end portion and an opposite, second end portion. The first end portion of each swing arm 14b or 14c is pivotally mounted to a respective one of the side rails 113 and 114 of the frame structure 110 through a pivot 15. The second end portion of at least one of the swing arms 14b and 14c is equipped with a first lifting wheel 25 and a second lifting wheel 24. The drawings of FIGS. 1 and 8-9 show only the second end portion of the swing arms 14b is equipped with a first lifting wheel 25 and a second lifting wheel 24. Practically, the second end portion of the swing arms 14c may also be equipped with the first lifting wheel 25 and the second lifting wheel 24. In addition, each of the pair of swing arms 14b and 14c may be reinforced by a pair of reinforcing pieces 14d rigidly connected to an end portion of the middle bar 14a on either side.

The back lifting actuator includes a motor member 26, an outer tube 26a extending from the motor member 26, and an activation rod 26b received in the outer tube 26a, engaged with the motor member 26 and configured to be telescopically movable relative to said outer tube 26a according to a direction of motor rotation. The motor member 26 is pivotally connected to the upper rail 111 of the frame structure 110 through a first bracket 26d. The activation rod 26b has a distal end portion pivotally connected to the middle bar 14a of the back lifting bracket 14 through a second bracket 26c.

The leg lifting assembly 130 has a leg lifting bracket 19 pivotally connected to the side rails 113 and 114 of the frame structure 110, and a leg lifting actuator 21 pivotally connected between the leg lifting bracket 19 and the lower rail 112 of the frame structure 110 for operably driving the leg lifting bracket 19 to pivotally move in an upward rotating direction or a downward rotating direction relative to the frame structure 110.

The leg lifting bracket 19 includes a middle bar 19a and a pair of swing arms 19b and 19c. The pair of swing arms 19b and 19c is transversely spaced and longitudinally extended, and rigidly connected to ends of the transversely extending middle bar 19a in an H-shaped form. Each of the pair of swing arms 19b and 19c has a first end portion and an opposite, second end portion. The first end portion of each swing arm 19b or 19c is pivotally mounted to a respective one of the side rails 113 and 114 of the frame structure 110 through a pivot 15a. The second end portion of at least one of the swing arms 19b and 19c is equipped with a leg lifting wheel 20. The drawings of FIGS. 1 and 8-9 show only the second end portion of the swing arms 19c is equipped with the leg lifting wheel 20. Practically, the second end portion of the swing arms 19b may also be equipped with the leg lifting wheel 20. In addition, each of the pair of swing arms 19b and 19c may be reinforced by a reinforcing piece rigidly connected to an end portion of the middle bar 19a on the side not pivotally mounted through a pivot 15a.

The leg lifting actuator includes a motor member 21, an outer tube 21a extending from the motor member 21, and an activation rod 21b received in the outer tube 21a, engaged with the motor member 21 and configured to be telescopically movable relative to said outer tube 21a according to a direction of motor rotation. The motor member 21 is pivotally connected to the lower rail 112 of the frame structure 110 through a first bracket 21d. The activation rod 21b has a distal end portion pivotally connected to the middle bar 19a of the leg lifting bracket 19 through a second bracket 21c.

In another embodiment, as shown in FIGS. 8-12, the frame structure 110 includes a back frame 13 and a leg frame 17 and a folding mechanism 16 connecting the back frame 13 and the leg frame 17 such that the back frame 13 and the leg frame 17 are pivotably foldable to one another at the folding mechanism 16. Preferably, the folding mechanism 16 is a hinge bracket. When folding the adjustable bed, the back frame 13 rotates around the rotation center of the folding mechanism 16 (FIG. 10). When the side of the back frame 13 touches the upper folding edge of the folding mechanism 16 (i.e., at a 90° position), the back frame 13 and the folding mechanism 16 continue to rotate around another rotation center (FIG. 11) until they overlap the leg frame 17. The upper folding edge of the folding mechanism 16 limits the position during the folding process. When the adjustable bed is completely folded, there is no gap between the back frame 13 and the leg frame 17, which minimizes the folded thickness. Other connecting means and other types of folding mechanism can also be utilized to practice the invention.

The back frame 13 includes an upper rail 13a, a lower rail 13b, and a pair of side rails 13c and 13d. The upper rail 13a and the lower rail 13b are longitudinally spaced and transversely extended, and the pair of side rails 13c and 13d is transversely spaced and longitudinally extended, and rigidly connected to the upper rail 13a and the lower rail 13b, such that the upper rail 13a and the lower rail 13b and the pair of side rails 13c and 13d are co-planar in a rectangle form. Preferably, the connection of the pair of side rails 13c and 13d to the upper and lower rails 13a and 13b is by welding ends of the upper rail 13a onto end portions of the pair of side rails 13c and 13d, and welding ends of the lower rail 13b onto opposite end portions of the pair of side rails 13c and 13d. Other connecting means can also be utilized to practice the invention.

The back lifting assembly 120 has a back lifting bracket 14 pivotally connected to the back frame 13, and a back lifting actuator pivotally connected between the back lifting bracket 14 and the back frame 13 for operably driving the back lifting bracket 14 to pivotally move in an upward rotating direction or a downward rotating direction relative to the back frame 13.

The back lifting bracket 14 includes a middle bar 14a and a pair of swing arms 14b and 14c. Each of the pair of swing arms 14b and 14c is in an arc-shaped design. The pair of swing arms 14b and 14c is transversely spaced and longitudinally extended, and rigidly connected to ends of the transversely extending middle bar 14a in an H-shaped form. Each of the pair of swing arms 14b and 14c has a first end portion and an opposite, second end portion. The first end portion of each swing arm 14b or 14c is pivotally mounted to a respective one of the side rails 13c and 13d of the back frame 13 through a pivot 15. The second end portion of at least one of the swing arms 14b and 14c is equipped with a first lifting wheel 25 and a second lifting wheel 24. The drawings of FIGS. 8-9 show only the second end portion of the swing arms 14b is equipped with a first lifting wheel 25 and a second lifting wheel 24. Practically, the second end portion of the swing arms 14c may also be equipped with the first lifting wheel 25 and the second lifting wheel 24. In addition, each of the pair of swing arms 14b and 14c may be reinforced by a pair of reinforcing pieces 14d (FIG. 8) rigidly connected to an end portion of the middle bar 14a on either side.

The back lifting actuator includes a motor member 26, an outer tube 26a extending from the motor member 26, and an activation rod 26b received in the outer tube 26a, engaged with the motor member 26 and configured to be telescopically movable relative to said outer tube 26a according to a direction of motor rotation. The motor member 26 is pivotally connected to the upper rail 13a of the back frame 13 through a first bracket 26d. The activation rod 26b has a distal end portion pivotally connected to the middle bar 14a of the back lifting bracket 14 through a second bracket 26c.

The leg frame 17 includes an upper rail 17a, a lower rail 17b, and a pair of side rails 17c and 17d. The upper rail 17a and the lower rail 17b are longitudinally spaced and transversely extended, and the pair of side rails 17c and 17d is transversely spaced and longitudinally extended, and rigidly connected to the upper rail 17a and the lower rail 17b, such that the upper rail 17a and the lower rail 17b and the pair of side rails 17c and 17d are co-planar in a rectangle form. Preferably, the connection of the pair of side rails 17c and 17d to the upper and lower rails 17a and 17b is by welding ends of the upper rail 17a onto end portions of the pair of side rails 17c and 17d, and welding ends of the lower rail 17b onto opposite end portions of the pair of side rails 17c and 17d. Other connecting means can also be utilized to practice the invention.

The leg lifting assembly 130 has a leg lifting bracket 19 pivotally connected to the leg frame 17, and a leg lifting actuator pivotally connected between the leg lifting bracket 19 and the leg frame 17 for operably driving the leg lifting bracket 19 to pivotally move in an upward rotating direction or a downward rotating direction relative to the leg frame 17.

The leg lifting bracket 19 includes a middle bar 19a and a pair of swing arms 19b and 19c. The pair of swing arms 19b and 19c is transversely spaced and longitudinally extended, and rigidly connected to ends of the transversely extending middle bar 19a in an H-shaped form. Each of the pair of swing arms 19b and 19c has a first end portion and an opposite, second end portion. The first end portion of each swing arm 19b or 19c is pivotally mounted to a respective one of the side rails 17c and 17d of the leg frame 17 through a pivot 15a. The second end portion of at least one of the swing arms 19b and 19c is equipped with a leg lifting wheel 20. The drawings of FIGS. 8-9 show only the second end portion of the swing arms 19c is equipped with the leg lifting wheel 20. Practically, the second end portion of the swing arms 19b may also be equipped with the leg lifting wheel 20. In addition, each of the pair of swing arms 19b and 19c may be reinforced by a reinforcing piece 19d (FIG. 9) rigidly connected to an end portion of the middle bar 19a on the side not pivotally mounted through a pivot 15a.

The leg lifting actuator includes a motor member 21, an outer tube 21a extending from the motor member 21, and an activation rod 21b received in the outer tube 21a, engaged with the motor member 21 and configured to be telescopically movable relative to said outer tube 21a according to a direction of motor rotation. The motor member 21 is pivotally connected to the lower rail 17b of the leg frame 17 through a first bracket 21d. The activation rod 21b has a distal end portion pivotally connected to the middle bar 19a of the leg lifting bracket 19 through a second bracket 21c.

The adjustable bed also includes middle leg brackets 27. One of the middle leg brackets 27 is connected to an end portion of the lower rail 13b closer to the side rail 13d. Another of the middle leg brackets 27 is connected to an end portion of the upper rail 17a closer to the side rail 17c.

As shown in FIG. 1, the plurality of platforms includes a back platform 1 movably disposed on the back lifting bracket 14; an upper seat platform 2 mounted on the back frame 13 and hinged with the back platform 1 through hinges 23; a lower seat platform 3 mounted on the leg frame 17 and being adjacent to the upper seat platform 2; a thigh platform 4 disposed on the leg lifting bracket and hinged with the lower seat platform 2 through hinges 23; and a leg platform 5 hinged with the thigh platform 4 through hinges 23. As such, the back platform 1 is operably rotatable around a lower side of the back platform 1 in a back platform forward direction (i.e., from a laid back or flat state to a lift state) or a back platform backward direction (i.e., from a lift state to a laid back or flat state); the thigh platform 4 is operably rotatable around the lower side of the thigh platform 4 in a thigh platform forward direction (i.e., from a laid back state to a lift state) or a thigh platform backward direction (i.e., from a lift state to a laid back state); and the leg platform 5 is operably rotatable around a rotating axis of the hinge 23.

In addition, a leg support member 22 is provided to support the leg platform 5. The term "platform" used herein refers to a bed board, board, or panel.

Specifically, the leg support member 22 has a first end pivotally connected to the side rails 17c and 17d of the leg frame 17, and an opposite, second end pivotally connected to the leg platform 5.

As shown in FIG. 1, the adjustable bed 100 further includes at least one massage assembly 6 for providing massage effects to a user of the bed. In the exemplary embodiment, two massage assembly 6 are used. Of them, one massage assembly 6 is disposed on the back platform 1 and the other is disposed on the leg platform 5.

Figure 6:
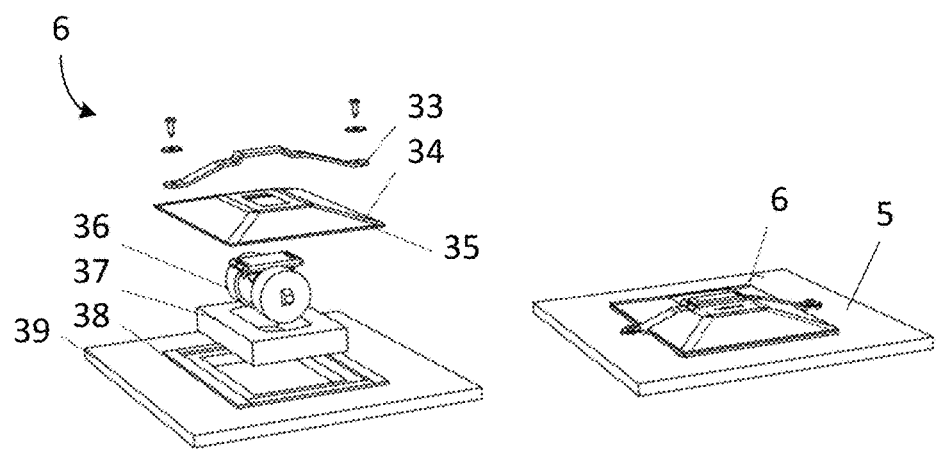
FIG. 6 shows schematically an exploded view and a perspective view of a massage assembly according to one embodiment of the invention.

As shown in FIG. 6, the massage assembly 6 includes a massage motor 36, an elastic belt 33, a massage motor cover 34, a velcro loop surface 35, a foam house 37, a velcro hook surface 38, and a plywood decking 39. The velcro loop surface 35 and the massage motor cover 34 are connected. A side of the massage motor 36 passes through an opening of the massage motor cover 34, and the elastic belt 33 passes through the side of the massage motor 36 (the side of the massage motor 36 has a small opening for the elastic belt to pass through) to connect the components as a whole. Further, the velcro hook surface 38 is fixed onto the plywood decking 39, which may be done by a nail or any other connecting means not limited thereto. The foam house 37 is placed inside a hole of the plywood decking 39, and the massage motor 36 as assembled above is placed inside a hole of the foam house 37 so that the velcro loop surface 35 and the velcro hook surface 38 are fit together. Finally, the massage motor 36 is fastened onto the plywood decking 39, e.g., via a pair of screws and a pair of washers. The massage motor 36 can be easily replaced by simply removing the elastic belt 33 from the side of the massage motor 36 and separating the velcro surfaces.

Figure 2:
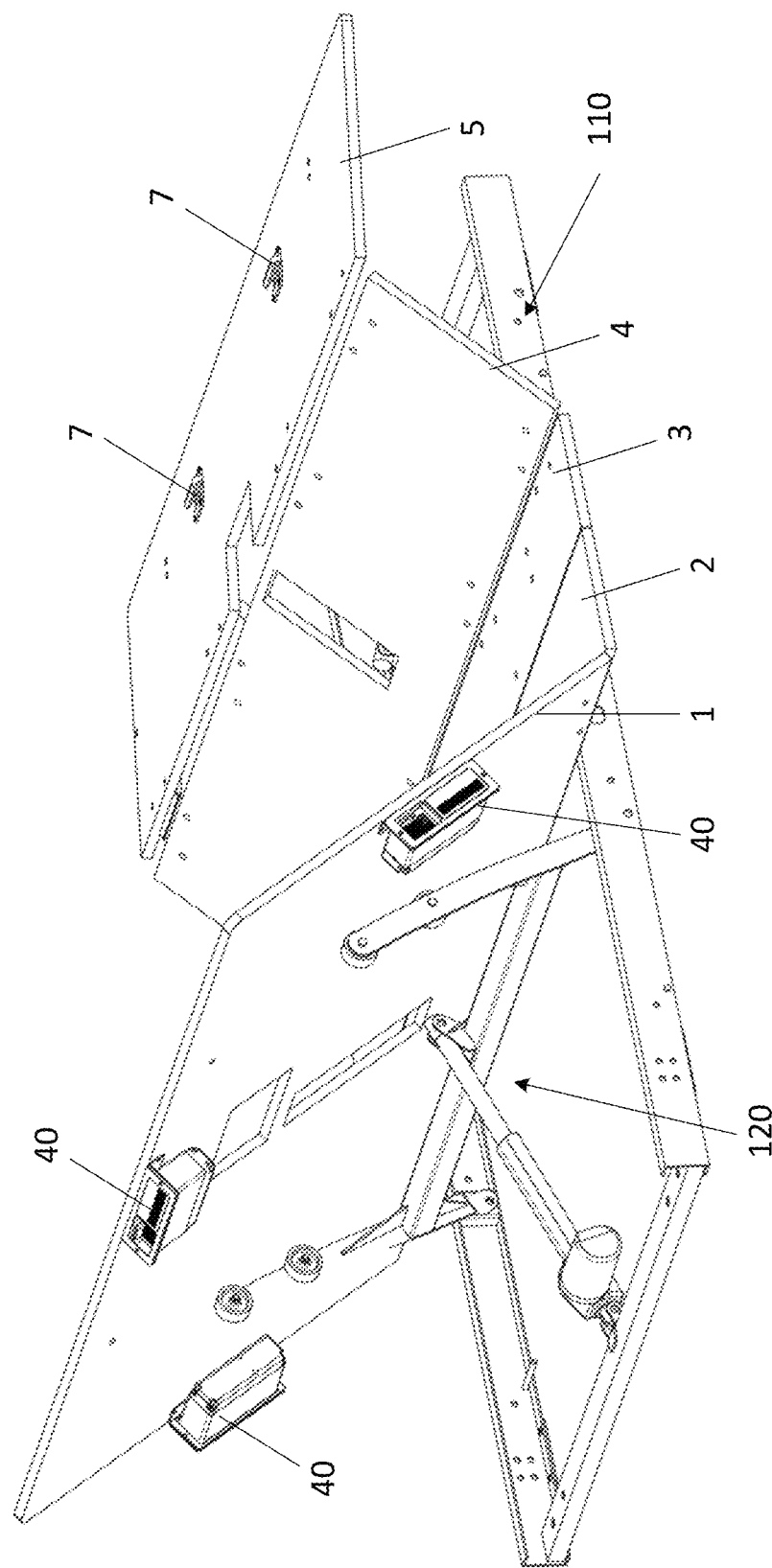
FIG. 2 shows schematically a front perspective view of an adjustable bed according to one embodiment of the invention.
Figure 7:
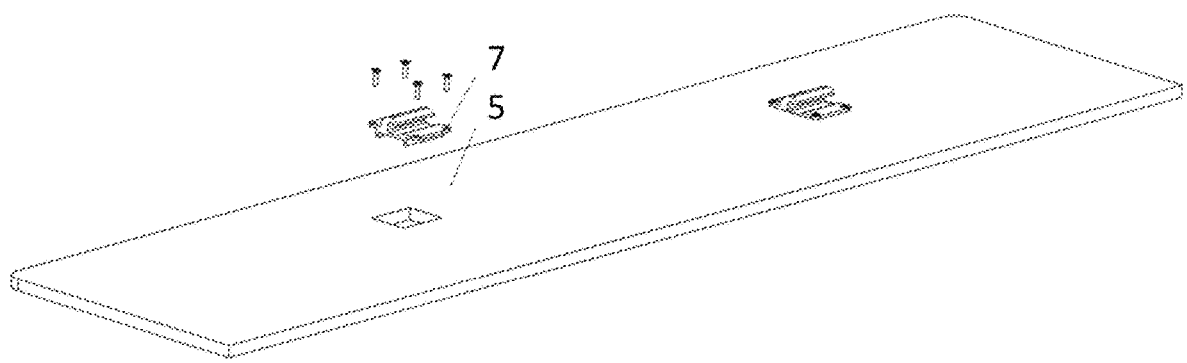
FIG. 7 shows schematically a mattress retainer bar holder attached onto a leg platform according to one embodiment of the invention.

As shown in FIGS. 2-3 and 7, the leg platform 5 is equipped with two mattress retainer bar holder 7 for retaining the mattress on the plurality of platforms 1-5.

The adjustable bed further includes a controller configured to control operations of the back lifting actuator and the leg lifting actuator, respectively, so as to lift individually or cooperatively the head lifting platform 1, the thigh platform 4, and the leg platform 5 in desired positions. A user lying on the adjustable bed can make adjustments as desired.

Figure 13:
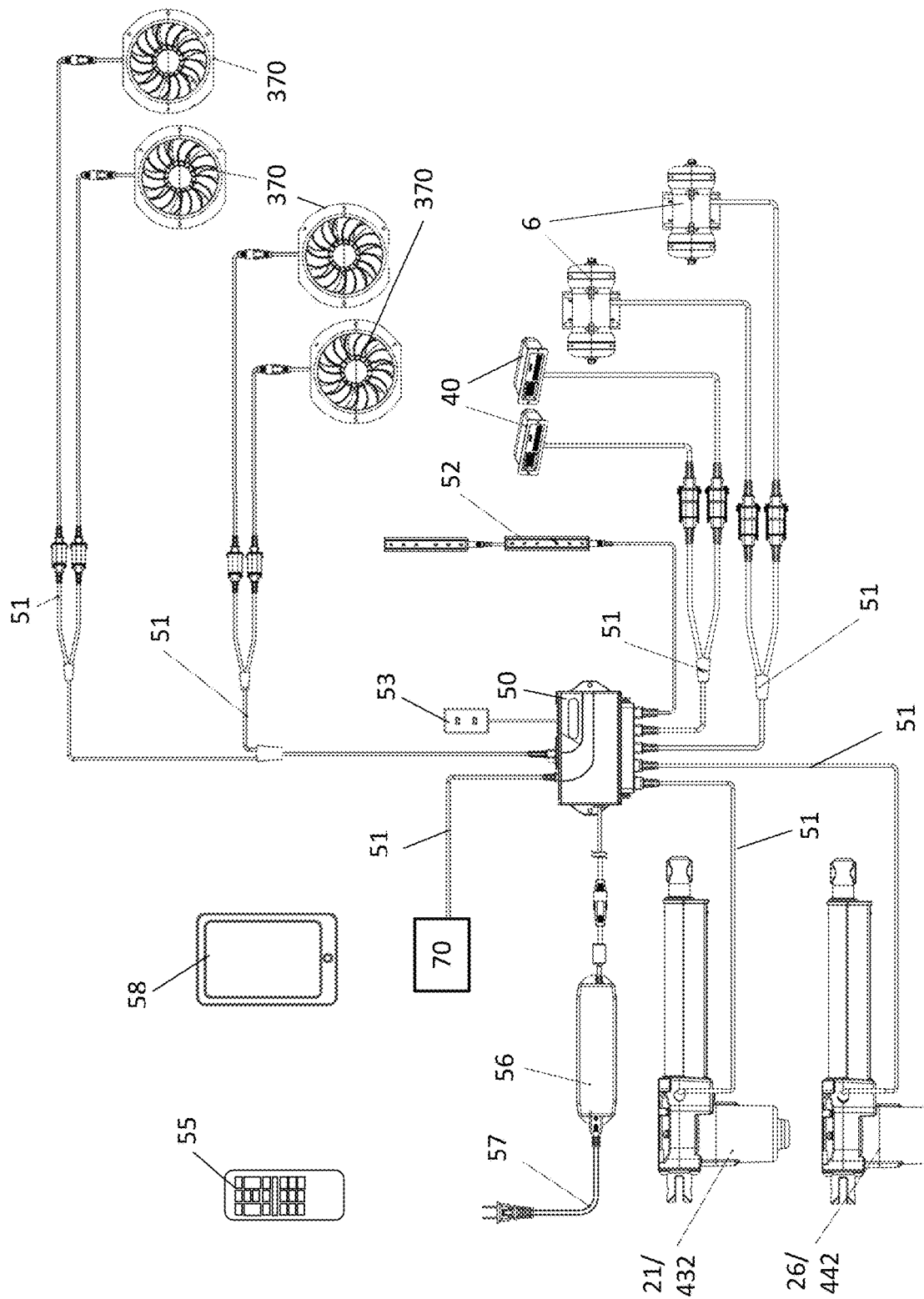
FIG. 13 shows schematically a control system according to one embodiment of the invention.

The adjustable bed system further includes a controlling system, which in one embodiment shown in FIG. 13, includes a controller 50 configured to control operations of the back lifting actuator (motor) 26, the leg lifting actuator (motor) 21, the aromatherapy system 40, the massage assembly 6, the fans 370, and the sensors 70, respectively, so as to lift individually or cooperatively the head lifting platform 1, the thigh platform 3, and the leg platform 5 in desired positions, to produce the fragrance in the surrounding space of the adjustable bed, and to provide the massage effects to the user. In one embodiment shown in FIG. 13, the control system includes a power cord 57, a power supply 56, a control box 50, a plurality of connecting cables 51, and LED lights 52. The control box (i.e., controller such as microcontroller unit or microprocessors) 50 is powered by the power supply 56 which is in turn connected to any power source via the power cord 57. The back lifting motor 26 and the leg lifting motor 21 are connected to the control box 50 via the plurality of connection cables e.g., the connecting cables 51. In this way, the user can adjust the bed position via a remote control 55 or an APP installed in the mobile device 58. Alternatively, LED lights 52 can be employed to indicate the working conditions of the back lifting motor 26 and the leg lifting motor 21. The term "APP", used herein the specification, refers to an application, especially as downloaded by a user to and installed in a mobile device, which a software program that is designed to perform specific functions directly for the user or, in some cases, for another application program or for operations of devices, such as the back lifting actuator (motor) 26, the leg lifting actuator (motor) 21, the aromatherapy system 40, the sensors 70, the massage assembly 6, fans 370, and/or LED lights 52 in the invention. The mobile device 58 can be a smart phone, a smart watch, a tablet, a laptop, or the likes.

FIG. 13 shows one exemplary embodiment of the controlling system with the controller 50 wiredly connected to the back lifting actuator (motor) 26, the leg lifting actuator (motor) 21, the aromatherapy system 40, the sensors 70, the massage assembly 6, the fans 370, and/or LED lights 52 through the connecting cables 51. In other embodiments, these connections of the controller 50 connected to the back lifting actuator (motor) 26, the leg lifting actuator (motor) 21, the aromatherapy system 40, the sensors 70, the massage assembly 6, the fans 370, and/or LED lights 52 are wireless connections through the Internet, WiFi®, Bluetooth®, a cellular network, and/or a mobile network.

Referring FIGS. 14-18, the mattress 200 is schematically shown according to one embodiment of the invention. The mattress includes a plurality of layers 210-250 vertically stacked to one another.

The plurality of layers includes a first layer 210, a second layer 220 disposed on the first layer 210, a third layer 230 disposed on the second layer 220, a fourth layer 240 disposed on the third layer 230; and a fifth layer 250 disposed on the fourth layer 240. It should be noted that other number of layers can also be utilized to practice the invention.

Figure 15:
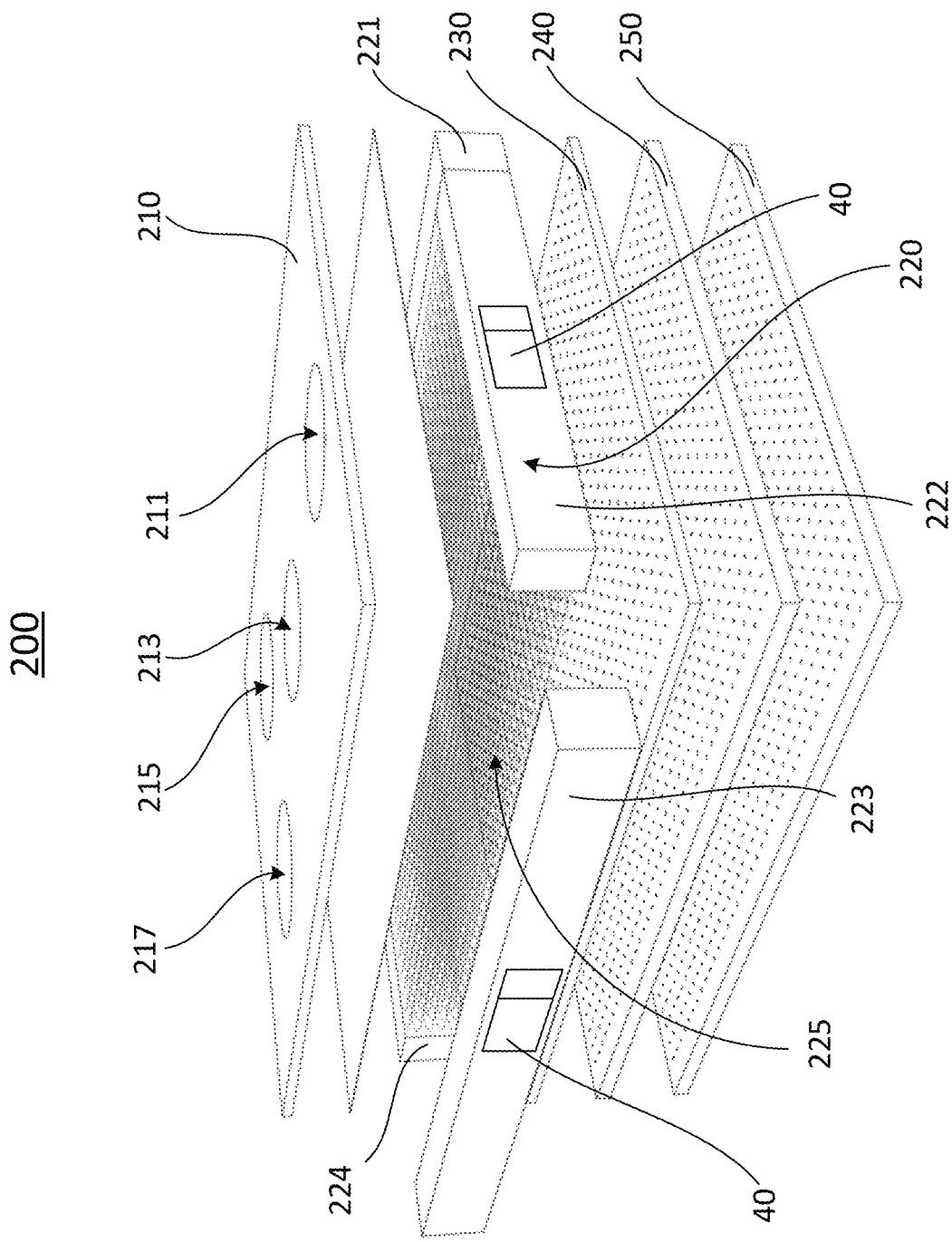
FIG. 15 shows schematically another exploded view of the mattress shown in FIG. 14.
Figure 16:
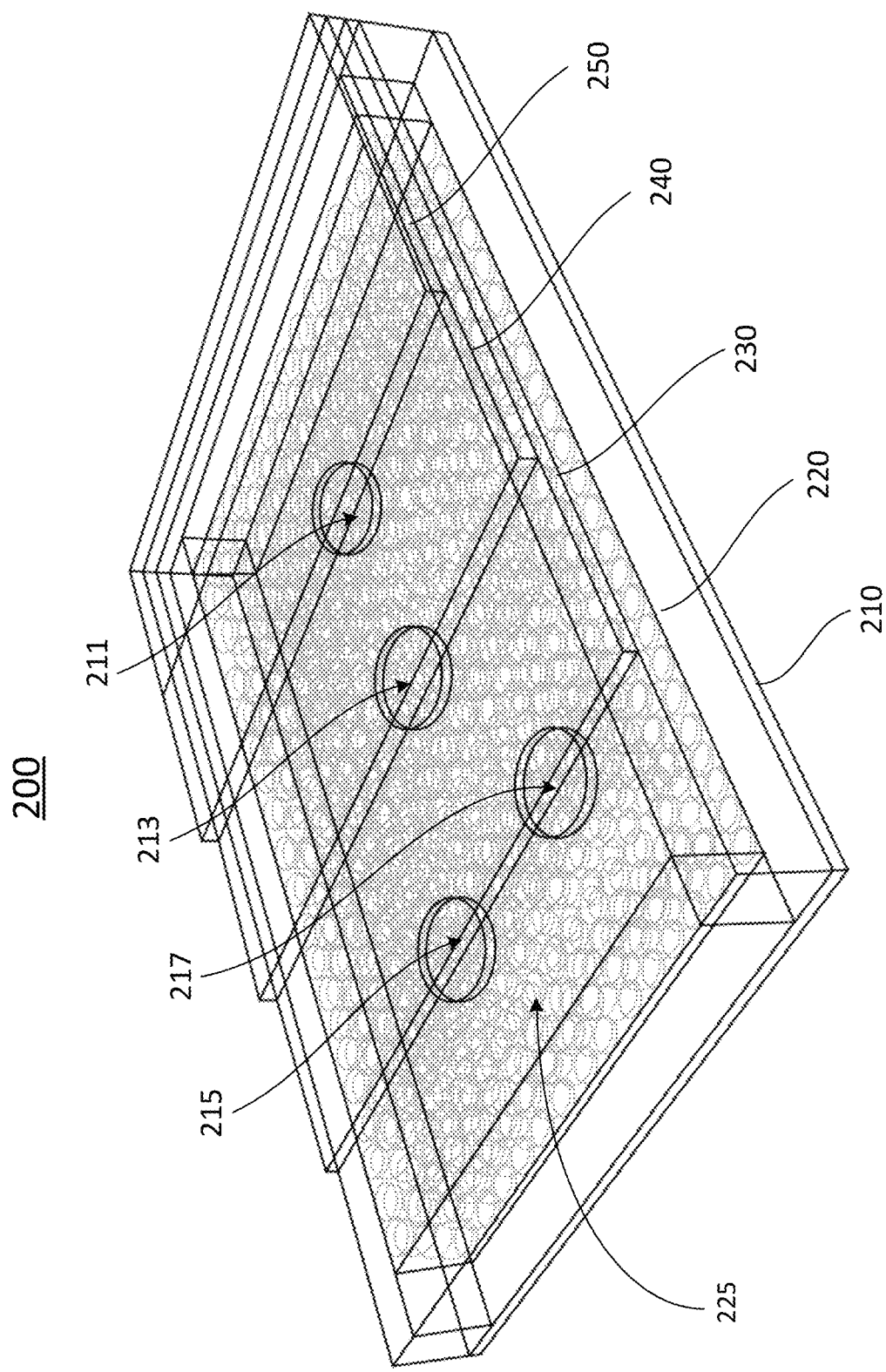
FIG. 16 shows schematically a partial cross-sectional and perspective view of the mattress shown in FIG. 14.
Figure 17:
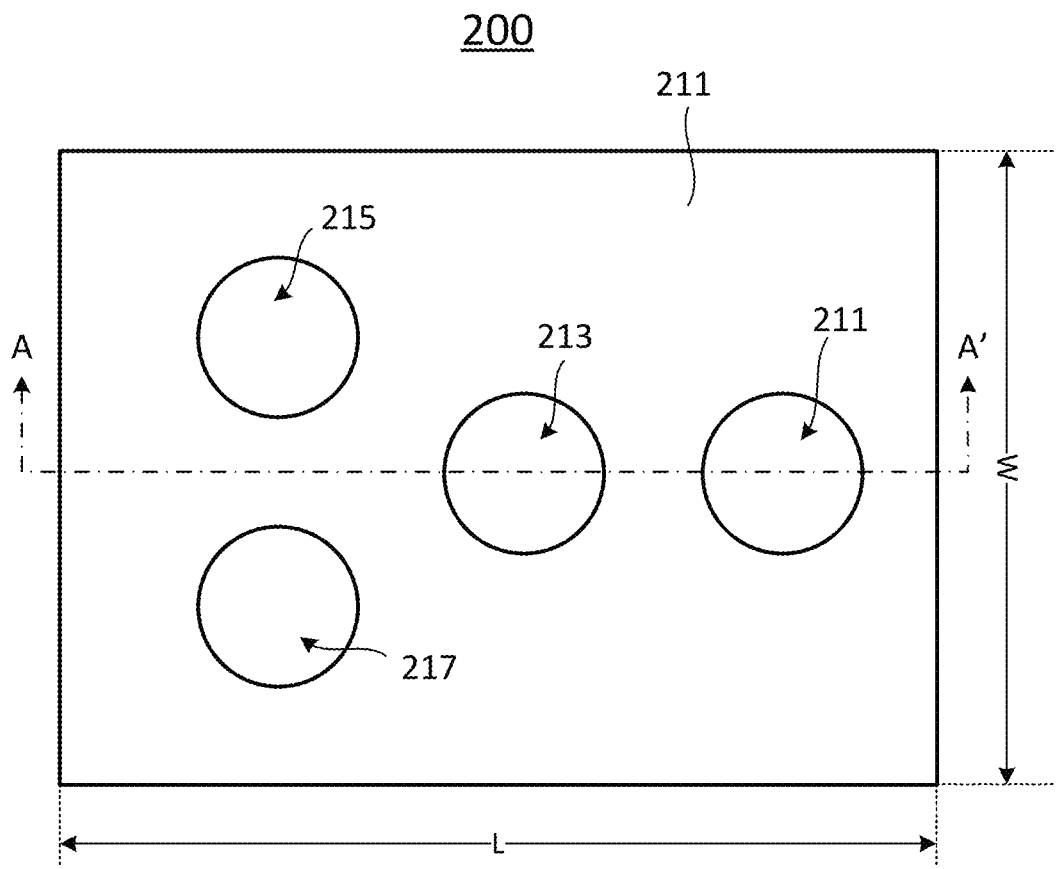
FIG. 17 shows schematically a bottom view of the mattress shown in FIG. 14.
Figure 18:
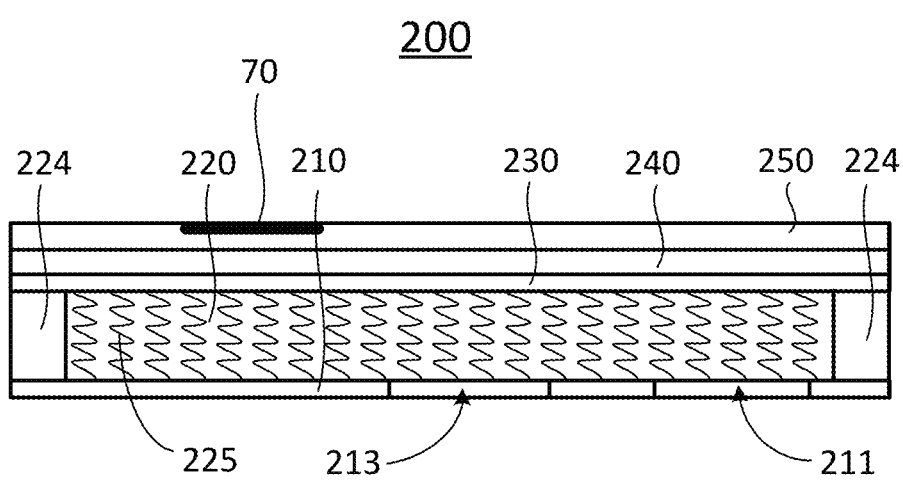
FIG. 18 shows schematically a cross-sectional view of the mattress along A-A' shown in FIG. 17.
Figure 21:
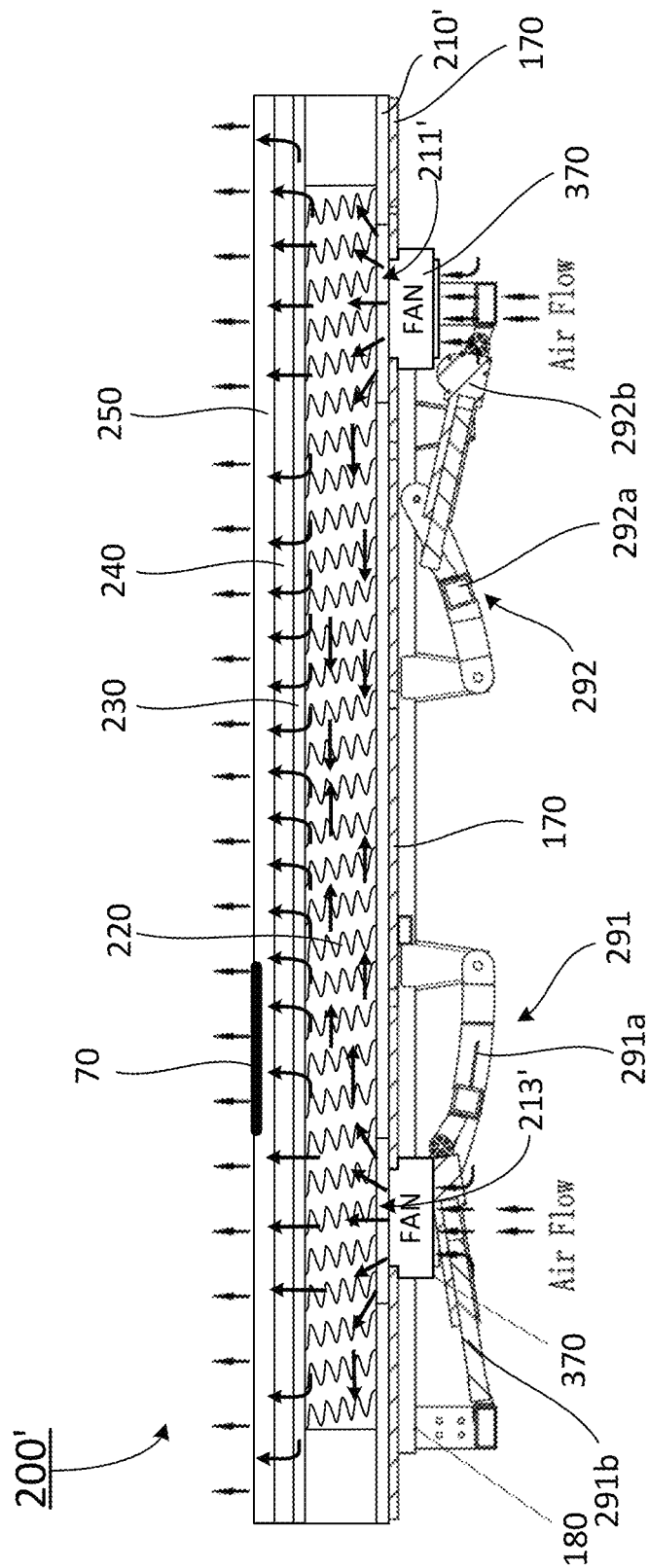
FIG. 21 shows schematically a cross-sectional view of an adjustable bed system with a mattress according to one embodiment of the invention.
Figure 22:
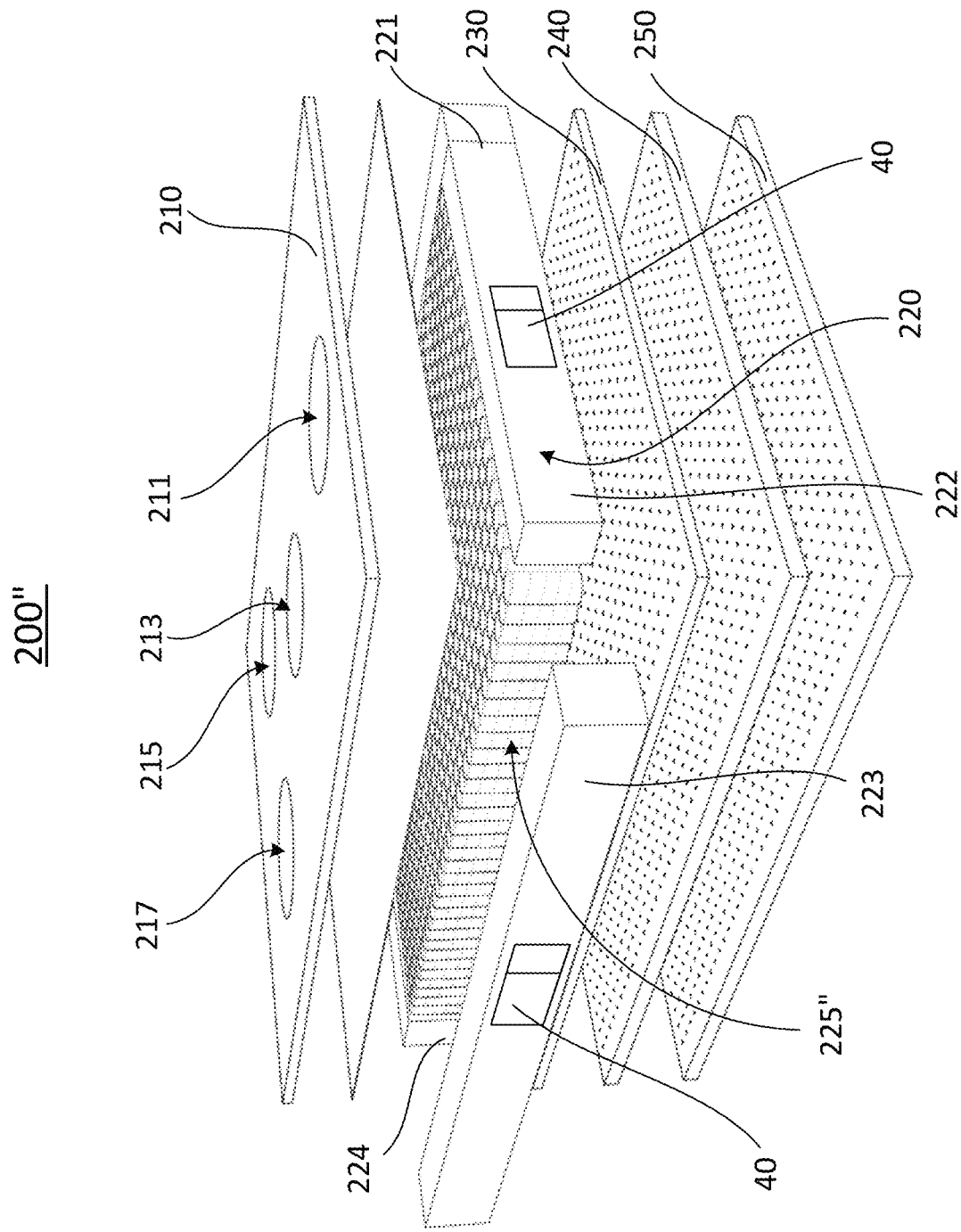
FIG. 22 shows schematically an exploded view of a mattress according to one embodiment of the invention.

As shown in FIG. 15-17, the first layer 210 comprises four openings 211-217 defined in the first layer 210. The openings 211-217 are operably in fluidic communication with a plurality of fans 370 for providing air circulation to a user through the mattress (FIG. 21). It should be noted that other number of openings can also be utilized to practice the invention. In some embodiments, the first layer 210 is formed of a flex support foam for providing corner to corner support, and ensuring a deeper, more regenerative night's sleep. In some embodiments, the first layer 210 has a thickness in a range of about 2-3 cm.

As shown in FIGS. 14-16, 18 and 22, the second layer 220 is arranged between the first layer 210 and the third layer 230 and comprises an array of springs 225. The array of springs comprises a specially fitted hybrid support-springs to provide breathable, ventilation and thorough foundation. In some embodiments shown in FIG. 22, the array of springs comprises a plurality of pocket springs 225", or coil springs, where the other layers of the mattress 200" is same as that of the mattress 200. In some embodiments, the array of springs comprises about 2500-2500 pocket springs, preferably 2000 pocket springs.

Figure 14:
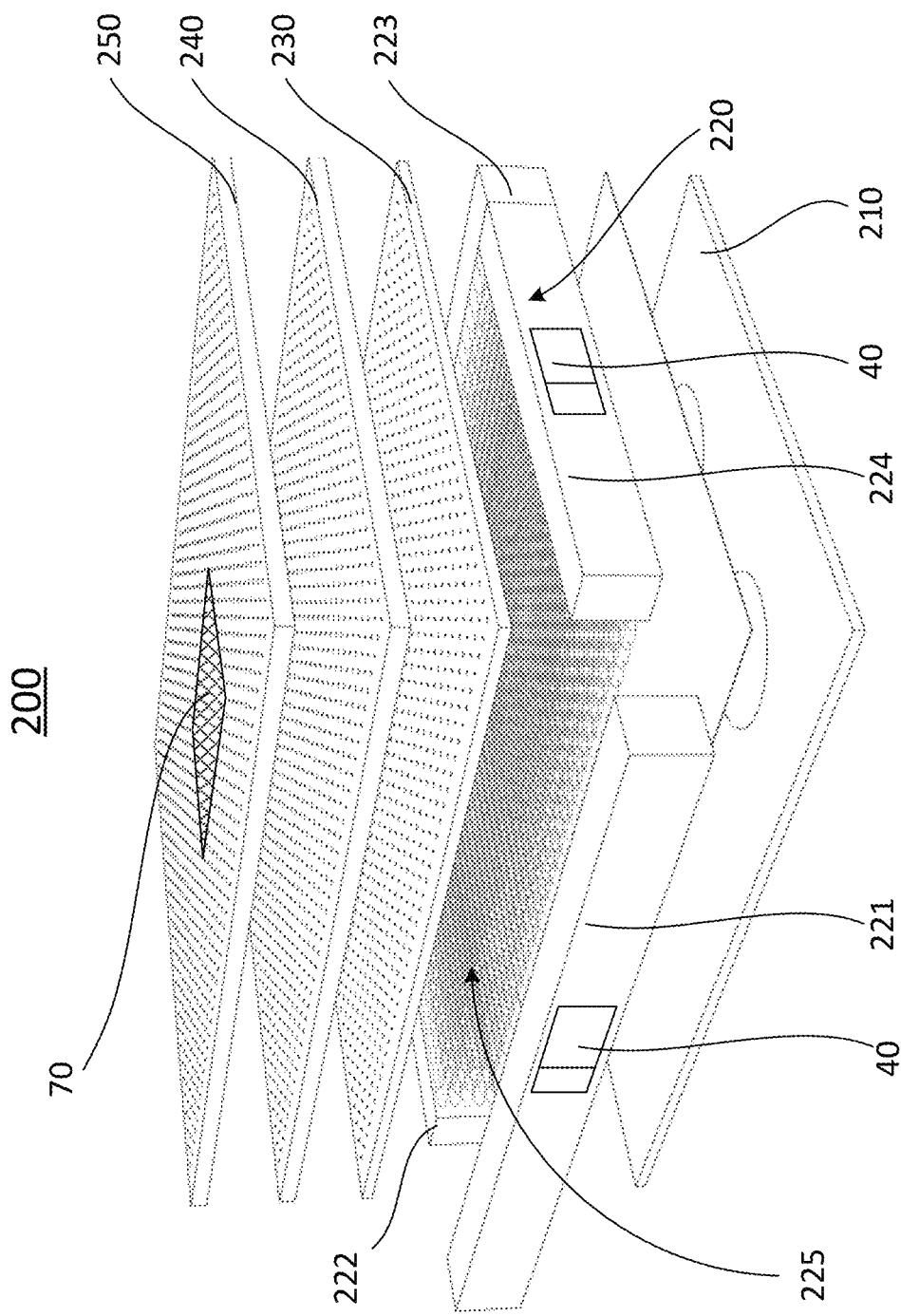
FIG. 14 shows schematically an exploded view of a mattress according to one embodiment of the invention.

As shown in FIGS. 14-16, the second layer 220 also has four side walls 221-224 defining a housing therewith for accommodating the array of springs 225. Each of the four side walls 221-224 can be formed of a flex support foam.

In some embodiments, the second layer 220 has a thickness in a range of about 22-20 cm.

The third layer 230 is formed of a flex comfort foam, which adds an additional layer of comfort to create a more breathable and supple feel.

In some embodiments, the third layer 230 has a thickness in a range of about 2-3 cm.

The fourth layer 240 is formed of a ventilated bamboo charcoal memory foam. The ventilated bamboo charcoal memory foam comprises a memory foam infused with bamboo charcoal, for regulating moisture, odor and/or temperature, and adapting to user body's individual points.

The fifth layer 250 is formed of a smart foam that is breathable, flexible and operably adapts to user body's natural contours. It also provides all of the benefits of the latex whilst being allergy free.

In some embodiments, each of the fourth layer 240 and the fifth layer 250 has a thickness in a range of about 2-5 cm.

In addition, the mattress 200 may also have a cool knit fabric cover for covering the plurality of layers 210-250, so as to enhance air-flow and breathability, creating a cooler, more deep sleep.

Figure 29:
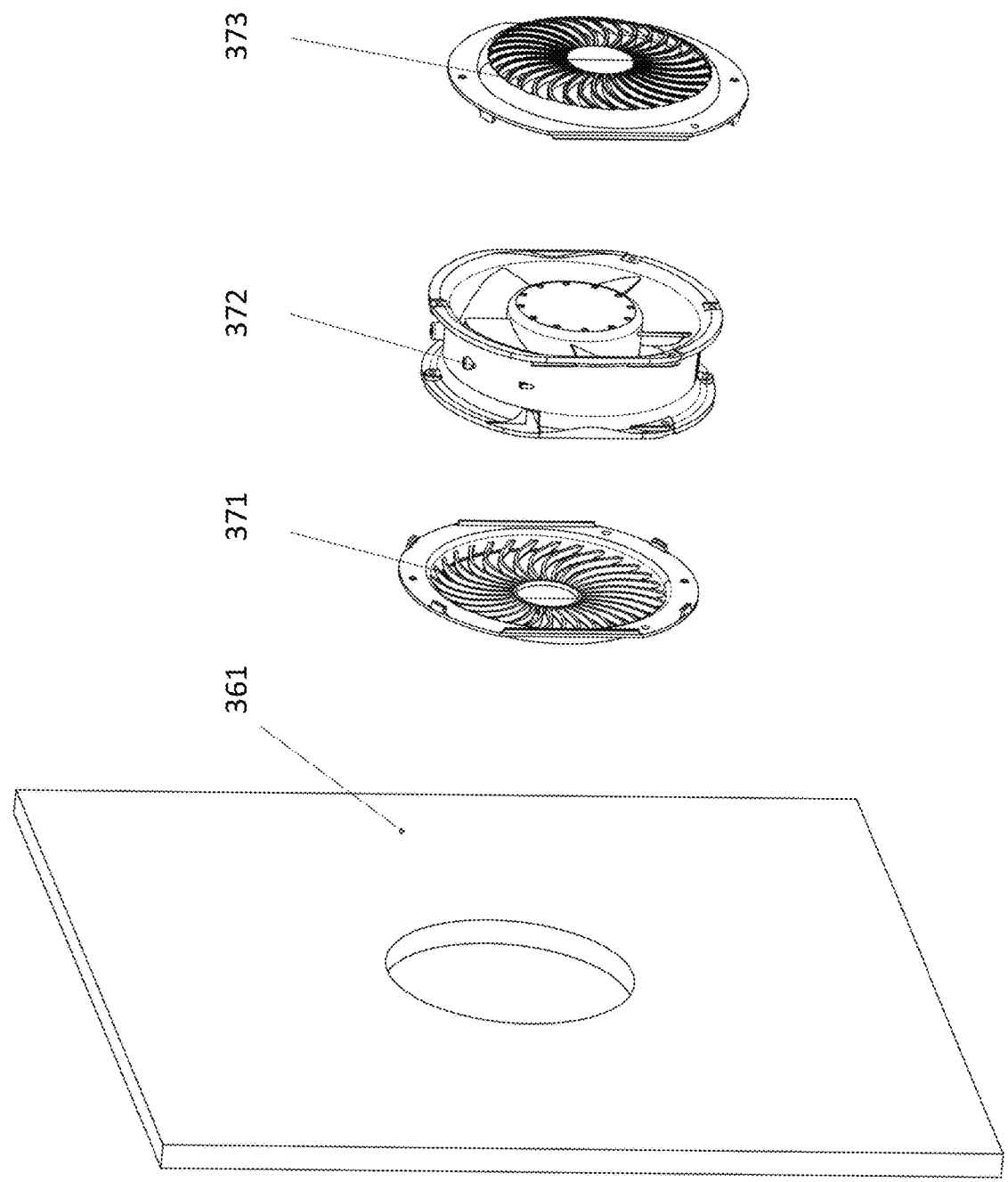
FIG. 29 shows schematically a fan according to one embodiment of the invention.

The mattress can be of any sizes, for example, a king size, a queen size, a full size, a twin size, or a customized size, by changing its width, W, and its length, L, as shown in FIGS. 17 and 29.

Furthermore, the mattress 200 also have the aromatherapy system 40 attached onto one or more of the plurality of layers 210-250 for producing desired fragrance in a surrounding space of the bed system so as to promote health and well-being of a user. In this exemplary embodiment as shown in FIGS. 14-15, the aromatherapy system 40 is placed in the four side walls 221-224 of the second layer 220.

In one embodiment, the aromatherapy system 40 is an electric aromatherapy system comprising one or more aromatherapy devices, wherein each aromatherapy device is configured to produce a fragrance when said aromatherapy device is turned on, wherein the fragrance is identical to or different from that produced by other aromatherapy device of the one or more aromatherapy devices.

In one embodiment, each aromatherapy device has one or more working modes, wherein the one or more working modes comprises a first working mode in which said aromatherapy device is turned on or turned off based on the user's instruction; a second working mode in which said aromatherapy device is turned on for a first period of time, and then turned off; and a third working mode in which said aromatherapy device is turned on for a second period of time regularly in a third period of time.

In one embodiment, each aromatherapy device comprises a container for containing an aromatic substance; a diffuser coupled to the container for operably heating the aromatic substance therein so as to produce the fragrance; and one or more indicators, each indicator for indicating one of the one or more working modes of said aromatherapy device.

In one embodiment, each aromatherapy device is controllable to operate in one of the one or more working modes by a remote control or an APP installed in a smart electronic device.

Further details of the aromatherapy system 40 are shown in FIG. 5 and described above and will be repeated herein.

In addition, as shown in FIG. 14, the mattress 200 also comprises one or more sensors 70 attached on one of plurality of layers 210-250 for measuring environment parameters of the surrounding space, and/or physiological parameters of the user during sleeping. The environment parameters of the surrounding space include moisture, odor and/or temperature. The physiological parameters of the user include a body temperature, a heart rate, and/or a respiratory rate.

In one exemplary embodiment shown in FIG. 14, the sensors 70 is disposed on the fifth layer 250, which may be operably in contact with the body of the user during sleeping.

In one embodiment, the sensors 70 comprise at least one of moisture sensors, odor sensors, temperature sensors, heart rate sensors, and respiratory rate sensors.

In one embodiment, the sensors 70 is in wired or wireless communications with a controller 50 (FIG. 13) that is configured to receive the measured environment parameters and/or the monitored physiological parameters from the sensors 70, process them therein, and wirelessly transmit the processed environment parameters and/or the processed physiological parameters to a database and/or a smart electronic device such as a smart phone, a smart watch, or a tablet.

The measured environment parameters can be used as a feedback for operations of the fans 370 (FIG. 21). For example, the moisture, odor and/or temperature meet a threshold, the controller 50 may control the fans to be turned on for air circulation, and turned off otherwise. The monitored physiological parameters can be used to monitoring the sleeping status/conditions including monitoring sleep disorders including insomnia, in which the user has difficulty falling asleep or staying asleep throughout the night, and sleep apnea, in which the user experiences abnormal patterns in breathing while the user is asleep. In addition, if the abnormal patterns in breathing occur, the controller 183 may send an alert to the smart electronic device to wake up the user or notice a caregiver for the user.

Figure 19:
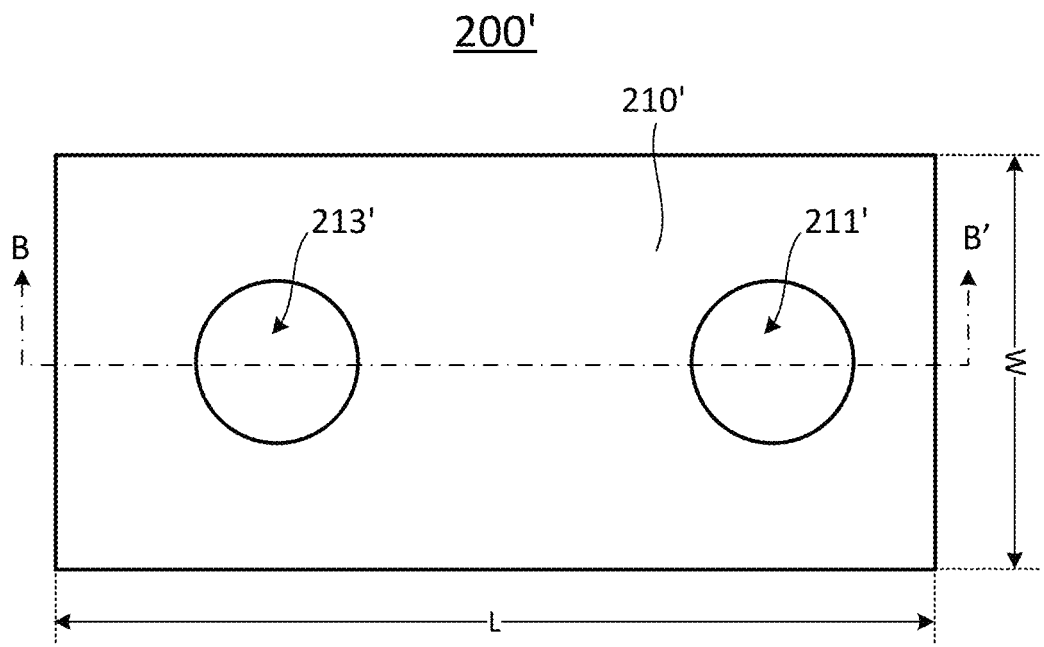
FIG. 19 shows schematically a bottom view of a mattress according to another embodiment of the invention.
Figure 20:
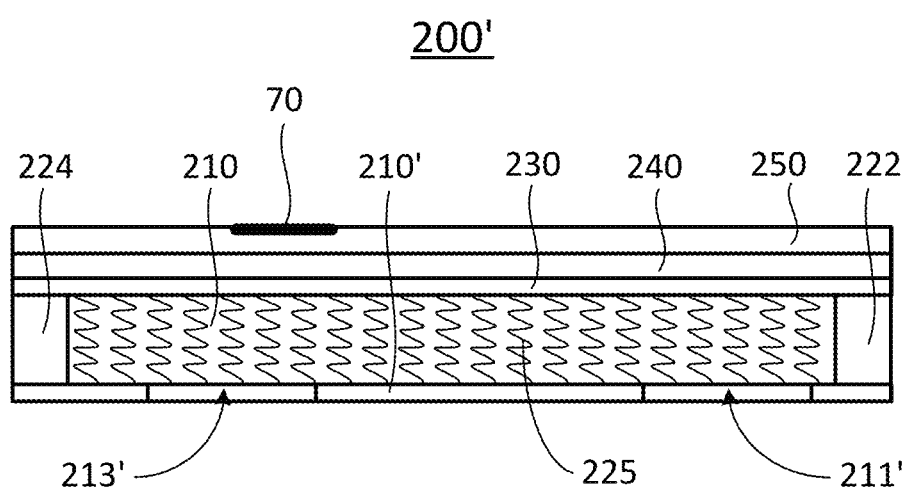
FIG. 20 shows schematically a cross-sectional view of the mattress along B-B' shown in FIG. 19.

FIGS. 19-20 shows schematically a mattress 200' according to another embodiment of the invention. The mattress 200' is similar to the mattress 200 shown in FIGS. 14-18, except that the size of the mattress 200' is different from that of mattress 200 and the first layer 210' has two openings 211' and 213' defined in the mattress 200'. It should be appreciated that other number of openings, e.g., one openings, three openings, five openings, six openings, seven openings, etc., can also be utilized to practice this invention.

Unlike traditional memory foam that may retain a user's heat, thereby causing the user to get hot during sleeping, the mattress according to the invention provides ventilation for superior airflow and temperature regulation. This added breathability means a user can rest more comfortably, so as to achieve maximum comfort during sleeping.

FIG. 21 shows schematically a cross-sectional view of an adjustable bed system with the mattress 200' according to one embodiment of the invention. The adjustable bed system includes a frame structure 280, one or more platforms (or bed boards) 270 moveably connected to the frame structure 280, a first lifting assembly 291 and a second lifting assembly 292 moveably connected to the frame structure 280.

One of the first lifting assembly 291 and the second lifting assembly 292 is a back lifting assembly, and the other of the first lifting assembly 291 and the second lifting assembly 292 is the leg lifting assembly. For the purpose of illustration, the first lifting assembly 291 is the back lifting assembly, while the second lifting assembly 292 is the leg lifting assembly 292. When the mattress 200' is disposed on the platforms 270, the upper (back) portion and the lower (leg) portion of the mattress 200' are in relation to the back lifting assembly 291 and the leg lifting assembly 292, respectively, and positions of the upper portion and the lower portion of the mattress 200' are individually and/or coordinately adjustable in accordance with operations of the back lifting assembly 291 and the leg lifting assembly 292.

The back lifting assembly 291 comprises a back lifting bracket 291*a* pivotally connected to the frame structure 280, and a back lifting actuator 291*b* pivotally connected between the back lifting bracket 291*a* and the frame structure 280 for operably driving the back lifting bracket 291*a* to pivotally move in an upward rotating direction or a downward rotating direction relative to the frame structure 280. Such pivotally moving of the back lifting bracket 291*a* causes the back portion of the platforms 270 and therefore the back portion of the mattress 210' to be lifted up (e.g., in a lift portion, not shown) or lifted down (e.g., in a flat position shown in FIG. 21).

The leg lifting assembly 292 comprises a leg lifting bracket 292*a* pivotally coupled to the frame structure 280, and a leg lifting actuator 292*b* pivotally connected between the leg lifting bracket 192*a* and the frame structure 280 for operably driving the leg lifting bracket 292*a* to pivotally move in an upward rotating direction or a downward rotating direction relative to the one of the frame structure. Such pivotally moving of the leg lifting bracket 292*a* causes the leg portion of the platforms 270 and therefore the leg portion of the mattress 210' to be lifted up (e.g., in a lift portion, not shown) or lifted down (e.g., in a flat position shown in FIG. 21).

The adjustable bed system also has two fans 370 that are mounted onto corresponding openings in the platforms 270, such that when the mattress 200' is placed on the platforms 270, the openings 211' and 213' in the first layer 210' of the mattress 200' are aligned with and are in fluidic commination with the two fans 370, respectively. In operation, the two fan 261 and 263 can individually or cooperatively move air (i.e., air flow or air circulation as indicated by arrows in FIG. 21) via the openings 211' and 213' into the mattress body and outputting the air from the top surface of the mattress 210'.

Specifically, each fan 261/263 is configured such that in operation, air is flown from the rear side of said fan 261/263 to the 211'/213' of the mattress 210', then spread through the mattress body and output from the sleeping surface (i.e., the top surface) of the mattress 210', as illustrated by arrows shown in FIG. 8. The air can be room temperature air, cooling air or heating air.

In addition, the strength of the air flow or air circulation is adjustable by individually or cooperatively operating the fans 370, based on the user's preference, and/or environment parameters measured by the sensors 70 as discussed above. The operation of the fans 370 can be automatically controlled, or manually controlled via a remote control. The operation can also be controlled via a remote control and/or an APP installed in a smart device such as a smart phone.

Figure 23:
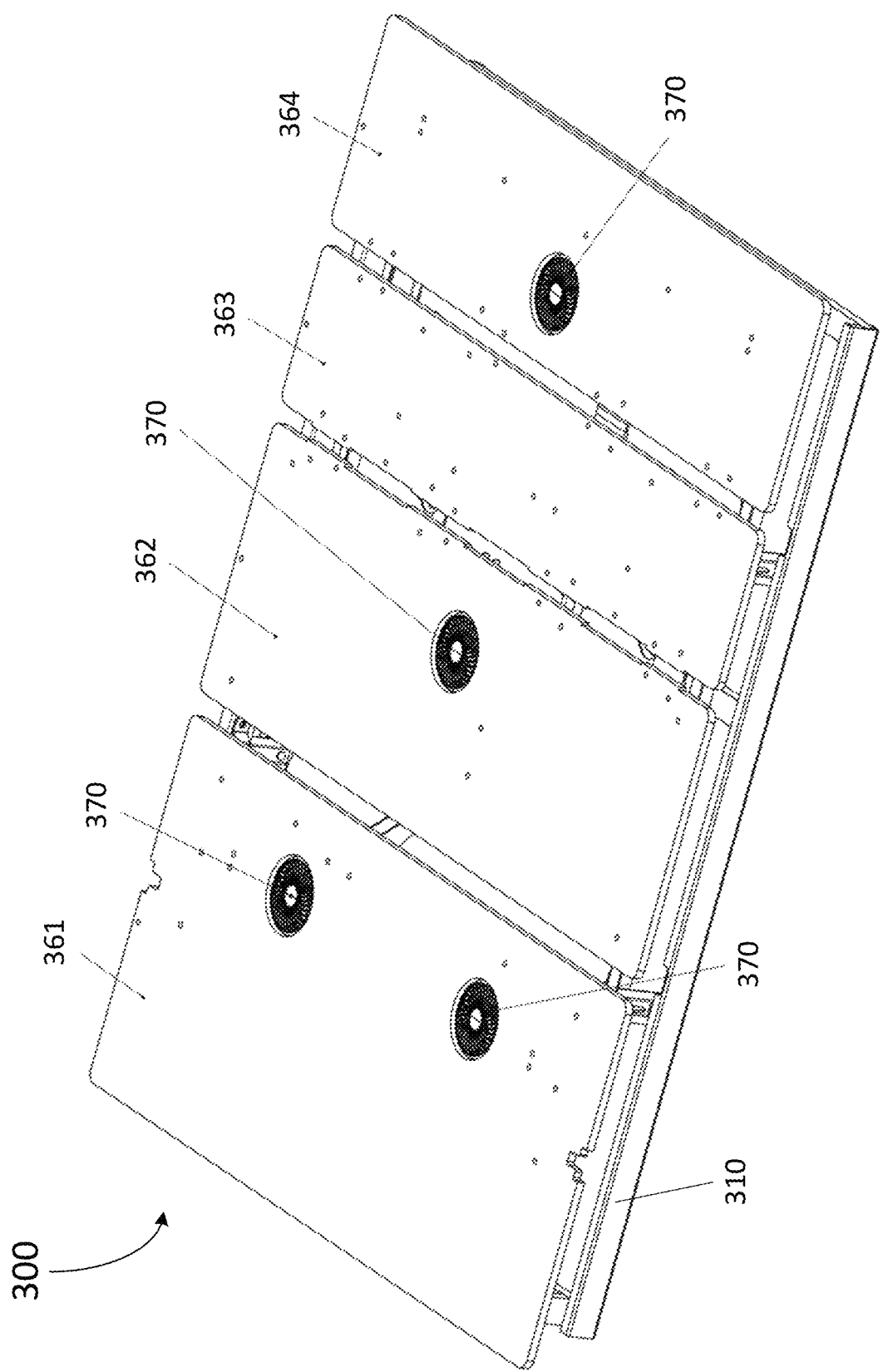
FIG. 23 shows schematically a front perspective view of an adjustable bed system in a flat state according to one embodiment of the invention.
Figure 24:
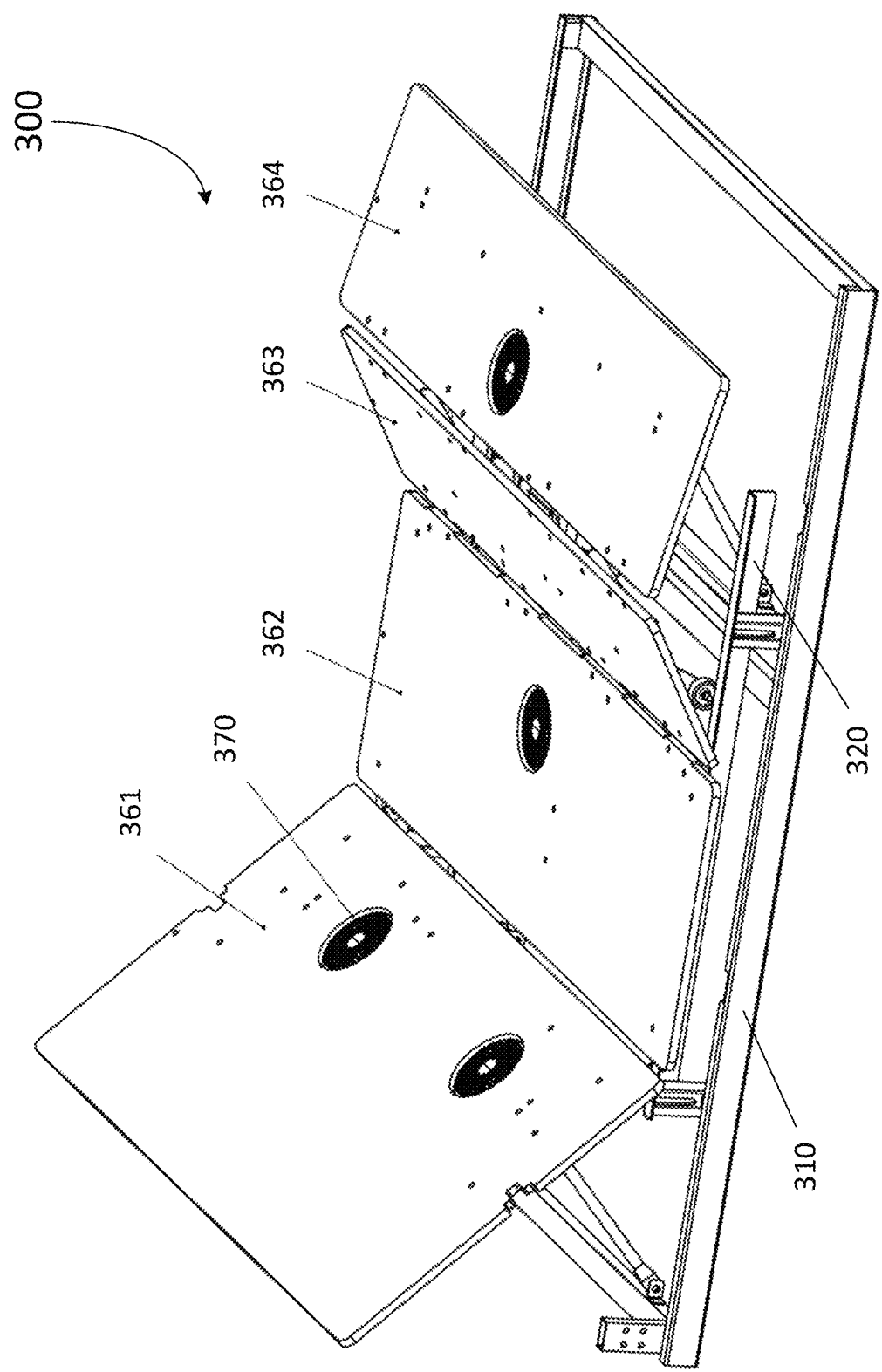
FIG. 24 shows schematically a front perspective view of the adjustable bed system shown in FIG. 23 in a lift state.
Figure 25:
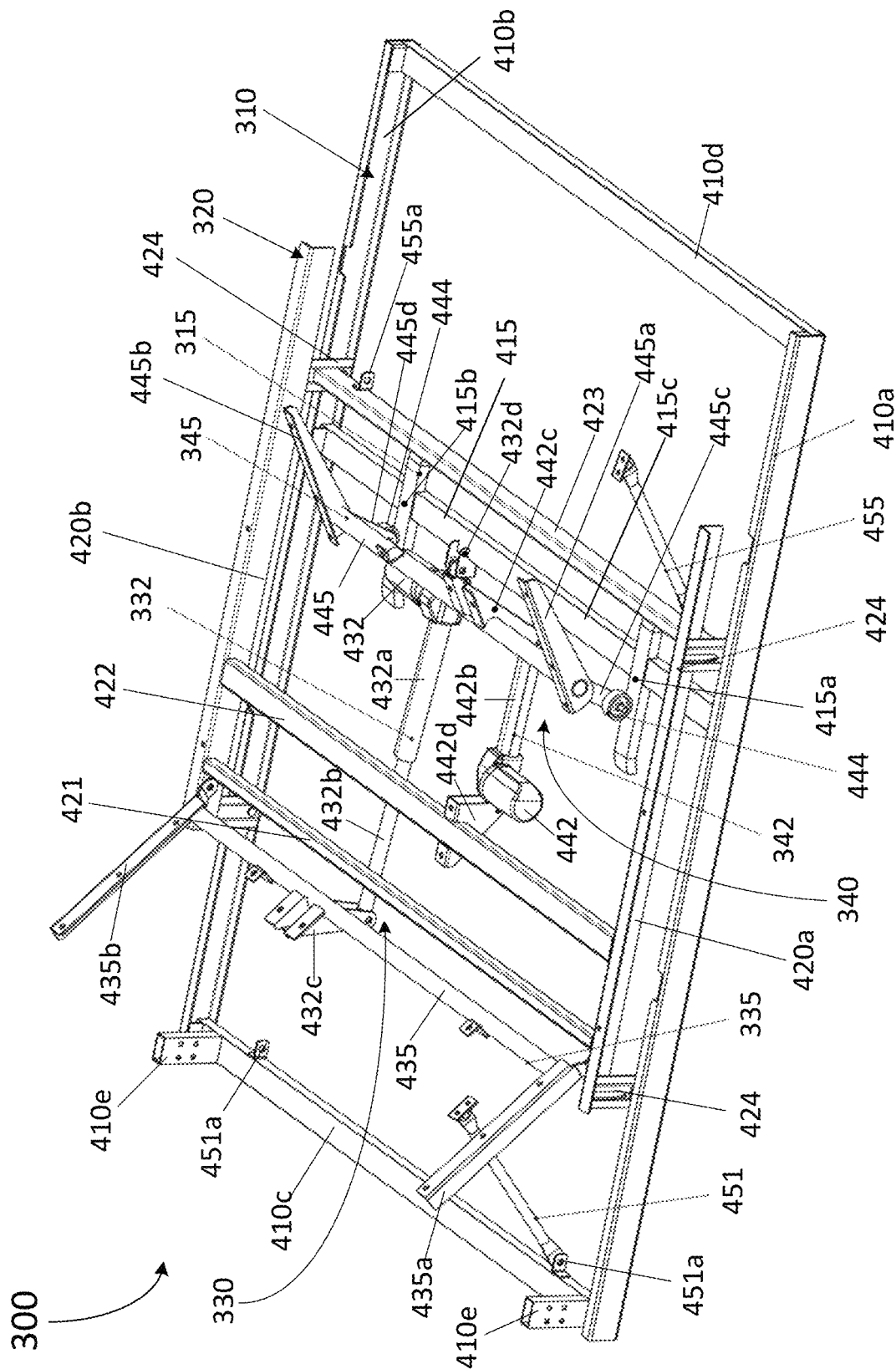
FIG. 25 shows schematically a front perspective view of the adjustable bed system shown in FIG. 23 in the lift state.
Figure 26:
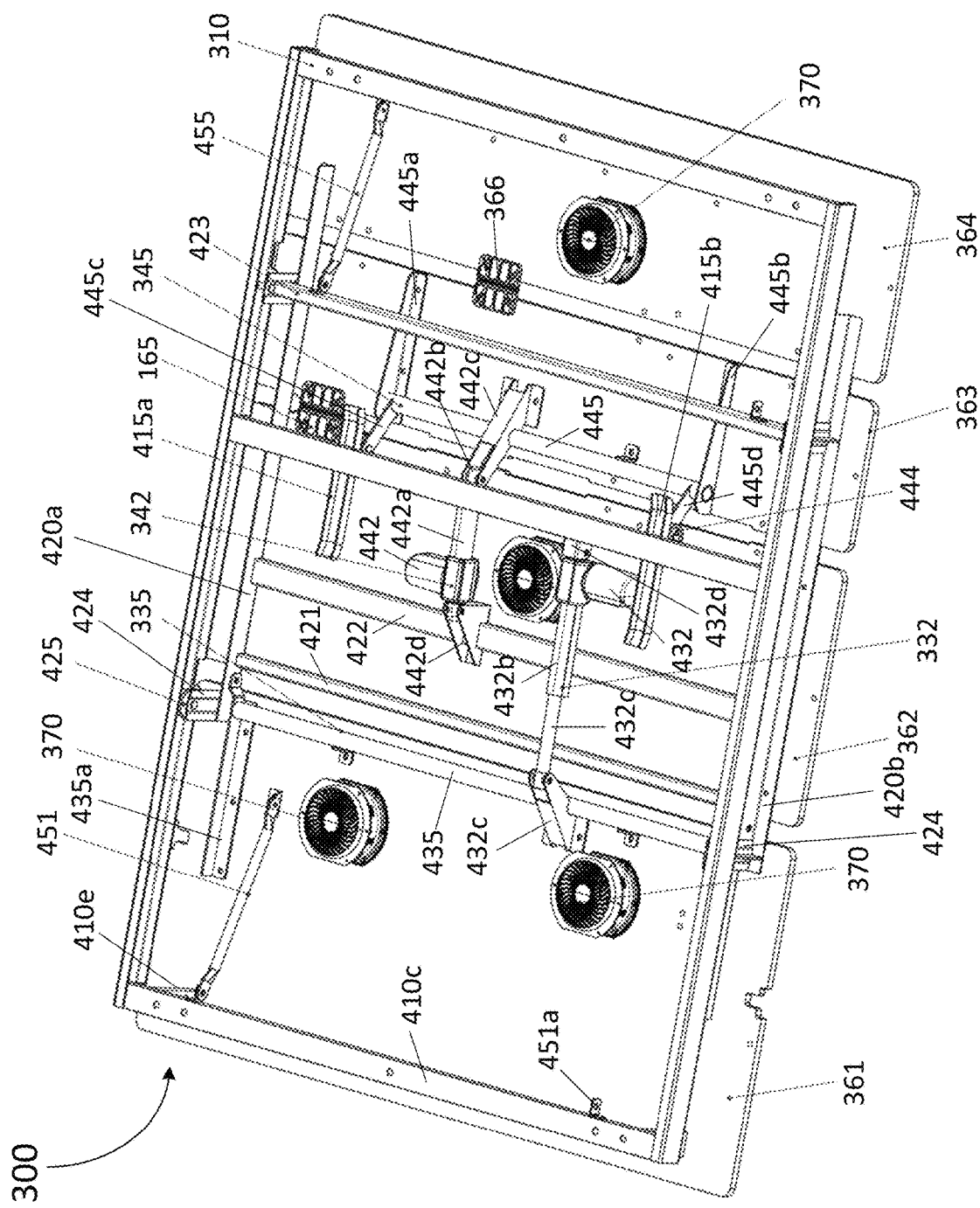
FIG. 26 shows schematically a rear perspective view of the adjustable bed system shown in FIG. 23 in the flat state.

Referring to FIGS. 23-29, and particularly to FIGS. 25-26, another embodiment of the adjustable bed system 300 includes a first frame structure 310; a second frame structure 320 disposed on and moveably coupled to the first frame structure 310; a back lifting assembly 330; a leg lifting assembly 340; a plurality of platforms 361-364; and a plurality of fans 370. The fans 370 can be same as or different from the fans 370 shown in FIG. 21.

The first frame structure 310 comprises two side rails 410*a* and 410*b* transversely spaced and longitudinally extended and being parallel to each other. Each side rail 410*a* or 410*b* has an upper end and opposite, lower end. In some embodiments, each side rail 410*a* or 410*b* is formed of a C-shape steel. In other embodiments, each side rail 410*a* or 410*b* is formed to have a trough or groove.

The first frame structure 310 also comprises an upper rail 410*c* and a lower rail 410*d* longitudinally spaced and transversely extended, where two ends of the upper rail 410*c* are connected to the upper ends of the two side rails 410*a* and 410*b* and two ends of the lower rail 410*d* are connected to the lower ends of the two side rails 410*a* and 410*b* such that the upper rail 410*c* and the lower rail 410*d* are parallel to each other.

Figure 27:
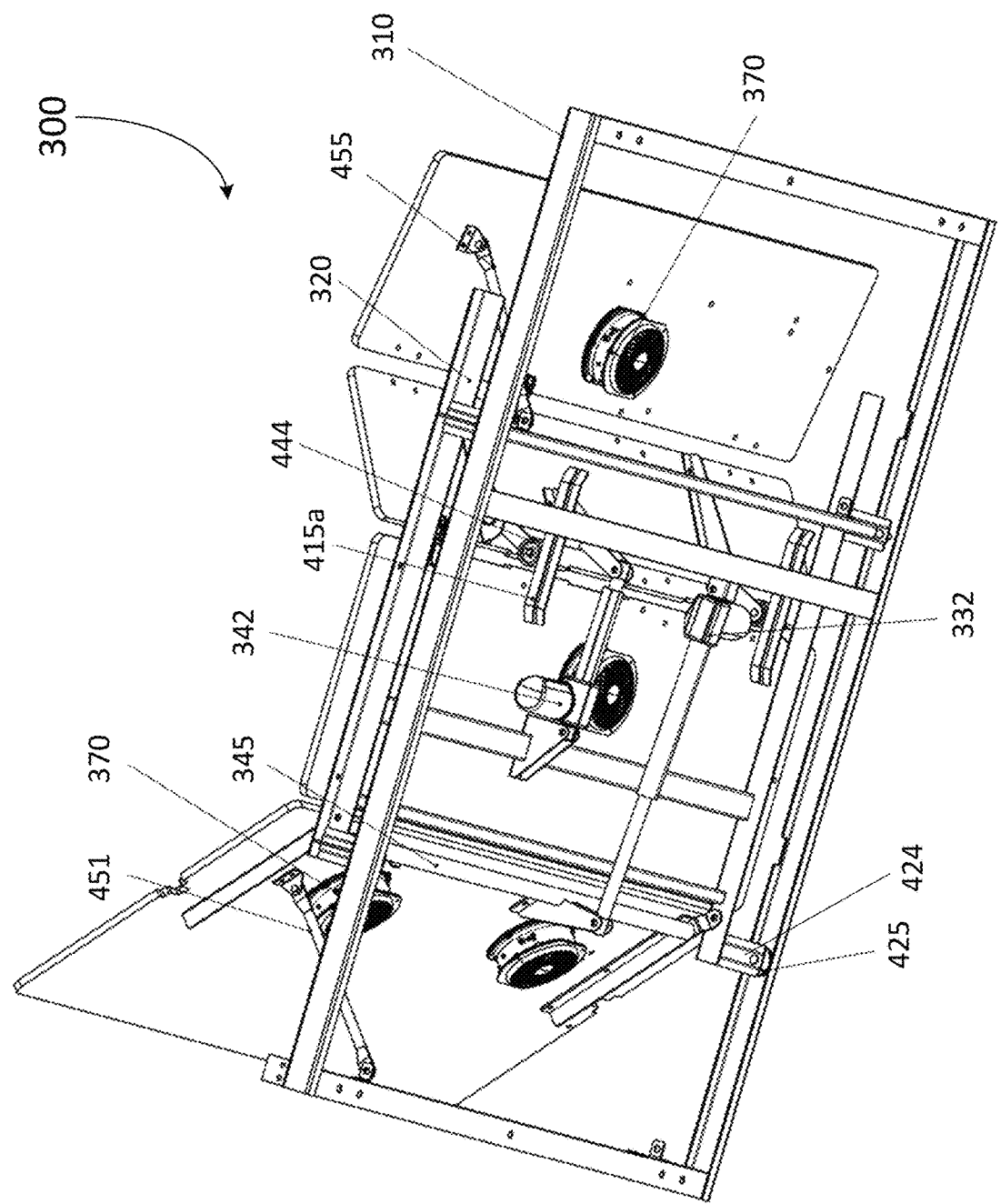
FIG. 27 shows schematically a rear perspective view of the adjustable bed system shown in FIG. 23 in the lift state.

The first frame structure 310 further comprises a support member 415 directly and fixedly connected to each of the two side rails 410*a* and 410*b* at a positon between the upper end and the lower end of said side rail 410*a* or 410*b*, without any intervening components present between the support member 415 and each of the two side rails 410*a* and 410*b*, such that there is a plane surface that the two side rails 410*a* and 410*b*, the upper rail 410*c*, the lower rail 410*d* and the support member 415 of the first frame structure 310 are all common, as shown in FIGS. 25-27. The direct and fixed connection can be achieved by welding for example. In some embodiments, the support member 415 includes a transversely-aligned bar 415*c* directly and fixedly connected to the two side rails 410*a* and 410*b*, and two longitudinally-aligned support arms 415*a* and 415*b* spaced-apart connected to the transversely-aligned bar 415*c*, as shown in FIG. 25. In one embodiment, the support member 415 is welded to the lower frame structure 310, that is, the support member 415 is directly and fixedly connected to the two side rails 410*a* and 410*b* of the lower frame structure 310.

The first frame structure 310 also includes two vertical posts 410*e* formed respectively on the two ends of the upper rail 410*c*, for supporting the back platform 361 when the adjustable bed system 300 is in a flat state.

In some embodiments, the connections between the two side rails 410a and 410b and the upper rail 410c, the lower rail 410d and the support member 415 are preferably by welding means. In addition to the welding means, other securing/connecting means, such as screwing means, mating connections, etc., can also be utilized to practice the invention.

The second frame structure 320 comprises two side rails 420a and 420b transversely spaced and longitudinally extended and being parallel to each other, and an upper rail 421, an intermediate rail 422 and a lower rail 423 connected to the two side rails 420a and 420b at an upper portion, an intermediate portion and a lower portion of the two side rails 420a and 420b, respectively.

Each side rail 420a or 420b of the second frame structure 320 has two spaced-apart, vertical posts 424 downwards extended into and moveably coupled to a respective one of the two side rails 410a and 410b of the first frame structure 310. For each side rail 420a or 420b of the second frame structure 320, the two spaced-apart, vertical posts 424 are located respectively at an upper end portion and a lower end portion of said side rail 420a or 420b. The vertical post 424 located at the lower end portion of said side rail 420a or 420b is moveable in the respective one of the two side rails 410a and 410b of the first frame structure 310 between the support member 415 and the lower end of the respective one of the two side rails 410a and 410b of the first frame structure 310. In some embodiments, the lower rail 423 is connected to the two vertical post 424 located at the lower end portions of the two side rail 420a or 420b. As such, during motion of the second frame structure 320 in the first frame structure 310 towards the front end portion of the two side rails 410a and 410b, the second frame structure 320 stops from moving when the lower rail 423 moves against the support member 415, and particularly against one ends of the two longitudinally-aligned support arms 415a and 415b.

In some embodiments, the lower end of each vertical post 424 is equipped with a roller 425. As assembled, the roller 425 is received and moveable in one of the two side rails 410a and 410b of the first frame structure 310. For example, the roller 425 is received and moveable in the C-shape steel, or the troughs/grooves of two side rails 410a and 410b.

The back lifting assembly 330 comprises a back lifting bracket 435 pivotally connected to the second frame structure 320, and a back lifting actuator 432 pivotally connected between the back lifting bracket 435 and the first frame structure 310 for operably driving the back lifting bracket 435 to pivotally move in an upward rotating direction or a downward rotating direction relative to one of the first frame structure 310 and the second frame structure 320.

The back lifting bracket 435 comprises a middle bar 435 and a pair of swing arms 435a and 435b. The pair of swing arms 435a and 435b is transversely spaced and longitudinally extended, and rigidly connected to ends of the transversely extending middle bar 435. Each of the pair of swing arms 435a and 435b has a first end portion and an opposite, second end portion. The first end portions of the pair of swing arms 435a and 435b are pivotally connected to the upper end portion of the two side rails 420a and 420b of the second frame structure 320, respectively. In one embodiment, the back lifting bracket 435 with the middle bar 435 and the pair of swing arms 435a and 435b are formed in an H-shape form or a U-shape form. Other designs of the back lifting bracket 435 can also be utilized to practice the invention.

The back lifting actuator 432 comprises a motor member 432, an outer tube 432a extending from the motor member 432, and an activation rod 432b having a first end portion received in the outer tube 432a and an opposite, second end portion. The activation rod 432b is engaged with the motor member 432 and configured to be telescopically movable relative to said outer tube 432a according to a direction of motor rotation. In the exemplary embodiment shown in FIGS. 25-27, the motor member 432 is pivotally connected to the support member 415 of the first frame structure 310 through a bracket 432d mounted to the transversely-aligned bar 415c of the support member 415, and the second end portion of the activation rod 432b pivotally connected to the middle bar 435 of the back lifting bracket 435 a bracket 432c mounted to the middle bar 435. In another embodiment, the motor member 432 is pivotally connected to the middle bar 435 of the back lifting bracket 435, and the second end portion of the activation rod 432b pivotally connected to the support member 415 of the first frame structure 310.

The leg lifting assembly 340 comprises a leg lifting bracket 345 pivotally coupled to the first frame structure 310, and a leg lifting actuator 342 pivotally connected between the leg lifting bracket 345 and the second frame structure 320 for operably driving the leg lifting bracket 345 to pivotally move in an upward rotating direction or a downward rotating direction relative to the one of the first frame structure 310 and the second frame structure 320.

The leg lifting bracket 345 comprises a middle bar 445 and a pair of swing arms 445a and 45b. The pair of swing arms 445a and 45b is transversely spaced and longitudinally extended, and rigidly connected to ends of the transversely extending middle bar 445. Each of the pair of swing arms 445a and 45b has a first end portion and an opposite, second end portion. The first end portions of the pair of swing arms 445a and 45b are disposed and moveable on the support member 415 of the first frame structure 310. In one embodiment, the first end portion of each swing arm 445a or 45b of the leg lifting bracket 345 is equipped with a leg lifting wheel 44 that is operably rotatable on one of the two longitudinally-aligned support arms 415a and 415b of the support member 415 of the first frame structure 310.

The leg lifting actuator 342 comprises a motor member 442, an outer tube 442a extending from the motor member 442, and an activation rod 442b having a first end portion received in the outer tube 442a and an opposite, second end portion. The activation rod 442b is engaged with the motor member 442 and configured to be telescopically movable relative to said outer tube 442a according to a direction of motor rotation. In the exemplary embodiment shown in FIGS. 25-27, the motor member 442 is pivotally connected to the intermediate rail 422 of the second frame structure 320 through a bracket 442d mounted to the intermediate rail 422, and the second end portion of the activation rod 432b pivotally connected to the middle bar 445 of the leg lifting bracket 345 through a bracket 442c mounted to the middle bar 445. In another embodiment, the motor member 442 is pivotally connected to the middle bar 445 of the leg lifting bracket 345, and the second end portion of the activation rod 442b pivotally connected to the intermediate rail 422 of the second frame structure 320.

In some embodiments, each of the motor members 432 and 442 includes a linear actuator.

The plurality of platforms 361-364 is coupled with the first frame structure 310, the second frame structure 320, the back lifting assembly 330 and the leg lifting assembly 340, such that positions of at least one or more of the plurality of platforms 361-364 are adjustable in accordance with operations of the back lifting assembly 330 and the leg lifting assembly 340.

Figure 28:
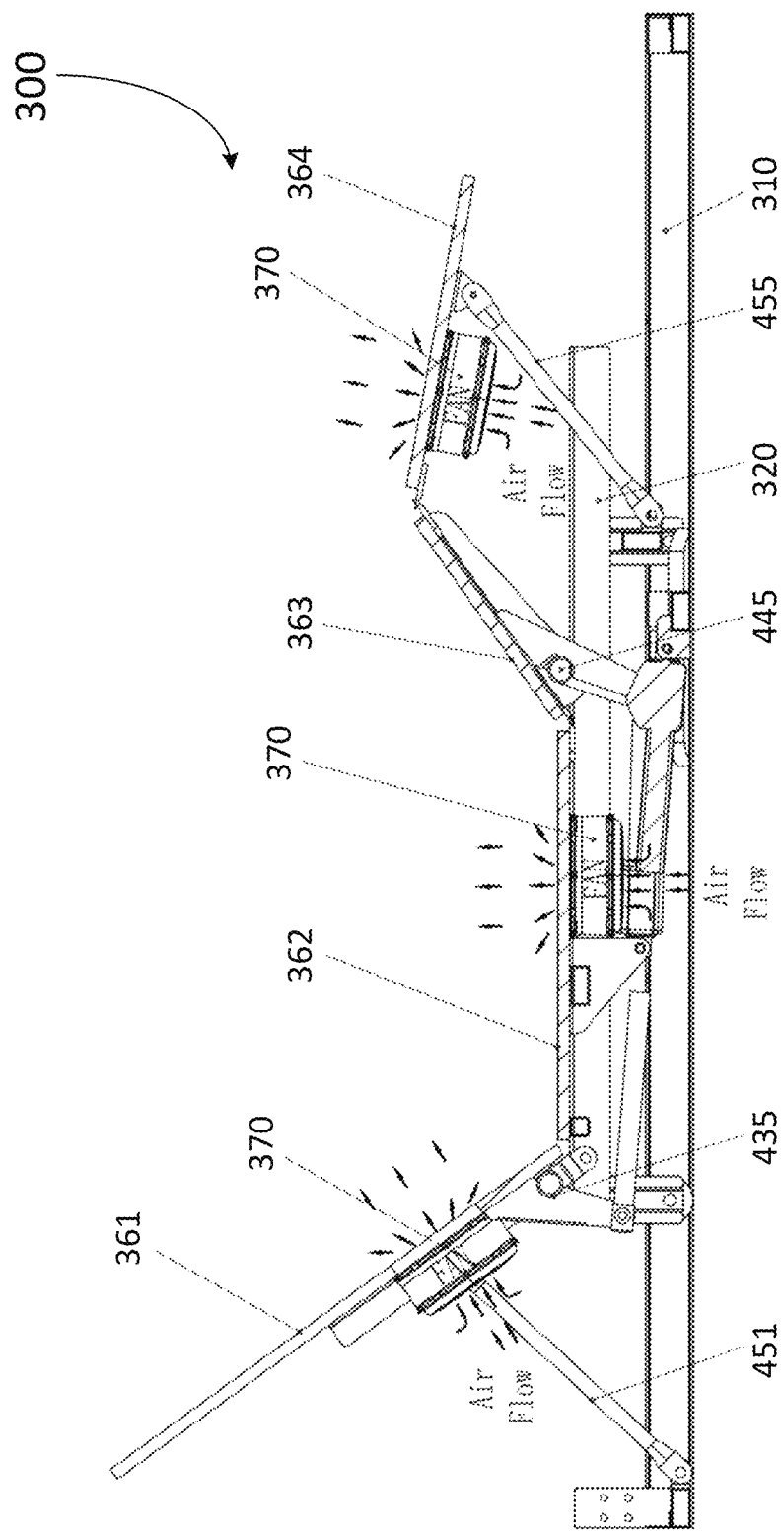
FIG. 28 shows schematically a cross-sectional view of the adjustable bed system shown in FIG. 24 in the lift state.

In the exemplary embodiment shown in FIGS. 23-24 and 28, the plurality of platforms 361-364 comprises a back platform 361, a seat platform 362, a thigh platform 363 and a leg platform 364, arranged in sequence from the upper side (i.e., near the upper rail 410c) to the lower side (i.e., near the lower rail 410c) of the adjustable bed system 300.

The back platform 361 is mounted on the back lifting bracket 435, such that the back platform 361 is operably rotatable around a lower side of the back platform 361 in a back platform forward direction (i.e., from a laid back or flat state to a lift state) or a back platform backward direction (i.e., from a lift state to a laid back or flat state). The seat platform 362 is mounted and fixed on the two side rails 420a and 420b of the second frame structure 320. The thigh platform 363 is mounted on the leg lifting bracket 345 with an upper side being hinged with a lower side of the seat platform 362 through a first hinge 365, such that the thigh platform 363 is operably rotatable around a rotating axis of the first hinge 365 in a thigh platform forward direction (i.e., from a laid back state to a lift state) or a thigh platform backward direction (i.e., from a lift state to a laid back state). The leg platform 364 with an upper side of the leg platform 364 being hinged with a lower side of the thigh platform 363 through a second hinge 366, such that the leg platform 366 is operably rotatable around a rotating axis of the second hinge 366.

In addition, the back lifting assembly 330 may also include a pair of back support tubes 451 for providing support to the back platform 361 when the adjustable be system 300 is in a lift state. Each back support tubes 455 has a first end pivotally connected to the upper rail 410c of the first frame structure 310 through a bracket 451a, and an opposite, second end pivotally connected to the back platform 361.

In one embodiment, the leg lifting assembly 340 also includes a pair of leg support tubes 455 for providing support to the leg platform 364 when the adjustable be system 300 is in a lift state, each leg support tubes 455 having a first end pivotally connected to the lower rail 423 of the second frame structure 320 through a bracket 455a, and an opposite, second end pivotally connected to the leg platform 364.

In some embodiments, one or more of the plurality of platforms 361-364 have a plurality of openings. In the exemplary embodiment shown in FIGS. 23-24 and 26-28, the back platform 361 has two openings, each of the seat platform 362 and the leg platform 364 has one opening. It should be noted that other arrangement of locations of the holes/openings can be also employed to practice the invention.

The plurality of fans 370 is mounted onto said one or more platforms 361-364 such that each of the plurality of openings accommodates a respective fan of the plurality of fans 370. Each of the plurality of fans 370 is adapted for operably providing air circulation in surrounding of the adjustable bed system 300. The air can be room temperature air, cooling air or heating air.

In one embodiment shown in FIG. 29, each of the fans 370 may include a fan motor assembly 372, a first fan cover 371, a second fan cover 373 and a plurality of mounting members. The first fan cover 371 and the second fan cover 373 cover two sides of the fan motor assembly 372 for protection. The plurality of mounting members mount the fan motor assembly 372, the first fan cover 371 and the second fan cover 373 to one of the back platform 361, the seat platform 362, the thigh platform 363 and the leg platform 364. In one embodiment, the plurality of mounting members are screws. Each of the fans 370 is configured such that in operation, air is flown from the rear side of said fan to a mattress not shown disposed on the plurality of platforms 370. The air can be room temperature air, cooling air or heating air.

In use, the adjustable bed system 300 also includes the mattress 200, 200' or 200" as shown in FIGS. 14-20 and 22. The mattress 200 or 200" is placed on and supported by the plurality of platforms 361-364, such that each opening 211, 213, 215 and 217 of the mattress 200 or 200" is directly aligned with a respective one of the fans 370, and a back portion and a leg portion of the mattress 200 or 200" are in relation to the back lifting assembly 330 and the leg lifting assembly 340, respectively, and positions of the back portion and the leg portion of the mattress 200 or 200" are individually and/or coordinately adjustable in accordance with operations of the back lifting assembly 330 and the leg lifting assembly 340.

In addition, the adjustable bed system 300 also includes the aromatherapy system 40 attached onto one or more of the platforms 361-364 (not shown).

The adjustable bed system 300 further also includes a controlling system, which one embodiment is shown in FIG. 13, includes a controller 50 configured to control operations of the back lifting actuator 432, the leg lifting actuator 342, the plurality of fans 370, the sensors 70, and the aromatherapy system 40, respectively, so as to lift individually or cooperatively the back platform 361, the thigh platform 363, and the leg platform 364 in desired positions, and to provide air and/or circulation, which can be room temperature air, cooling air or heating air. In one embodiment shown in FIG. 13, the control system includes a power cord 57, a power supply 56, a control box 50, a plurality of connecting cables 51, LED lights 52 and USB ports 52. The control box 50 is powered by the power supply 56 which is in turn connected to any power source via the power cord 57. The fans 370, the back lifting motor member 432 and the leg lifting motor member 442, the sensors 70 and the aromatherapy system 40 are connected to the control box 50 via the plurality of connection cables 51. In this way, the user can adjust the bed position, air flow strength of each cooling fan system and/or the aromatherapy system from the remote control 55 and/or the mobile device 58 in which the APP for controlling the operations is installed. Alternatively, LED lights 52 can be employed to indicate the working conditions of the fans 370, the back lifting motor 432 and the leg lifting motor 442. For example, when one of the cooling fan system 370 is working, the corresponding one of the LED lights 52 is turned on and emits green light. The USB ports 53 are set for interfacing with the control box 50 by the user when needed.

FIG. 13 shows one exemplary embodiment of the controlling system with the controller 50 wiredly connected to the back lifting motor 432 and the leg lifting motor 442, the aromatherapy system 40, the sensors 70, the massage assembly 6, the fans 370, and/or LED lights 52 through the connecting cables 51. In other embodiments, these connections of the controller 50 connected to t the back lifting motor 432 and the leg lifting motor 442, the aromatherapy system 40, the sensors 70, the massage assembly 6, the fans 370, and/or LED lights 52 are wireless connections through the Internet, WiFi®, Bluetooth®, a cellular network, and/or a mobile network.

According to the invention, the adjustable bed system 300 with power fans has at least following benefits.

All the bed components (i.e., the back lifting assembly 330, the leg lifting assembly 340, the platforms 361-364 and mattress on the platforms) are coupled with the second (upper) frame structure 320, and the upper frame structure 320 is equipped with four rollers 425 that are received in the C-shape steel structure of the first (lower) frame structure 310. When the back lifting actuator 432 operably pushes the back lifting bracket 435 to rotate, the pulling force of the pair of back support tubes 451 causes the upper frame structure 320 to slide back and forth in the C-shaped steel of the lower frame structure 310 through the rollers 425, thereby realizing the forward or backward movement of the top portion (i.e., the back lifting assembly 330, the leg lifting assembly 340, the platforms 361-364 and mattress on the platforms) of the adjustable bed system 300.

The leg lifting assembly 330 is equipped with the rollers 444 that are moveably disposed on the roller support member 415, which in one embodiment is welded to the lower frame structure 310. Since the rollers 444 are supported by the support member 415, which increases the strength of the bed system, even if the bed system is subjected to force/stress, no deformation will occur.

Opening holes in the back platform 361, the seat platform 362, and the leg platform 364 of the bed system for mounting the fans, and the air flow of the fans can be adjusted according to the needs of the user.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

What is claimed is:

1. A bed system, comprising:
    a frame structure;
    a plurality of platforms disposed on the frame structure; and
    an adjustable assembly coupled with the frame structure and the plurality of platforms for operably adjusting one or more of the plurality of platforms in desired positions;
    a plurality of fans mounted onto openings in the plurality of platforms and adapted for operably providing air circulation in a surrounding space of the bed system; and
    an aromatherapy system attached onto one or more of the plurality of platforms for producing desired fragrance in the surrounding space so as to promote health and well-being of a user,
    wherein the adjustable assembly comprises:
        a back lifting assembly comprising a back lifting bracket pivotally connected to the frame structure, and a back lifting actuator pivotally connected between the back lifting bracket and the frame structure for operably driving the back lifting bracket to pivotally move in an upward rotating direction or a downward rotating direction relative to the frame structure; and
        a leg lifting assembly comprising a leg lifting bracket pivotally connected to the frame structure, and a leg lifting actuator pivotally connected between the leg lifting bracket and the frame structure for operably driving the leg lifting bracket to pivotally move in an upward rotating direction or a downward rotating direction relative to the frame structure,
    wherein the back lifting bracket comprises a middle bar and a pair of swing arms, wherein the pair of swing arms is transversely spaced and longitudinally extended, and rigidly connected to ends of the transversely extending middle bar, and each of the pair of swing arms has a first end portion and an opposite, second end portion, wherein the first end portion of each swing arm is pivotally mounted to the frame structure; and
    wherein the back lifting actuator comprises a motor member, an outer tube extending from the motor member, an activation rod received in the outer tube, engaged with the motor member and configured to be telescopically movable relative to said outer tube according to a direction of motor rotation, wherein the motor member is pivotally connected to the frame structure, and the activation rod has a distal end portion pivotally connected to the middle bar of the back lifting bracket, or wherein the motor member is pivotally connected to the middle bar of the back lifting bracket, and the activation rod has a distal end portion pivotally connected to the frame structure.

2. The bed system of claim 1, wherein the aromatherapy system is an electric aromatherapy system comprising one or more aromatherapy devices, wherein each aromatherapy device is configured to produce a fragrance when said aromatherapy device is turned on, wherein the fragrance is identical to or different from that produced by other aromatherapy device of the one or more aromatherapy devices.

3. The bed system of claim 2, wherein each aromatherapy device has one or more working modes, wherein the one or more working modes comprises
    a first working mode in which said aromatherapy device is turned on or turned off based on the user's instruction;
    a second working mode in which said aromatherapy device is turned on for a first period of time, and then turned off; and
    a third working mode in which said aromatherapy device is turned on for a second period of time regularly in a third period of time.

4. The bed system of claim 3, wherein each aromatherapy device is controllable to operate in one of the one or more working modes by a remote control and/or an APP installed in a smart electronic device.

5. The bed system of claim 1, further comprising a mattress comprising a plurality of layers vertically stacked to one another, the plurality of layers comprising at least a first layer having a plurality of openings defined therein and being operably in fluidic communication with the plurality of fans for providing air circulation to a user through the mattress, wherein the mattress is placed on the plurality of platforms such that each opening in the first layer of the mattress is directly aligned with and is in fluidic commination with a respective one of the plurality of fans.

6. The bed system of claim 5, wherein the mattress further comprises one or more sensors attached on one of the plurality of layers for measuring environment parameters of the surrounding space, and/or physiological parameters of the user during sleeping, wherein the environment parameters of the surrounding space include moisture, odor and/or temperature, and the physiological parameters of the user include a body temperature, a heart rate, and/or a respiratory rate.

7. The bed system of claim 6, wherein the one or more sensors is in wired or wireless communications with a controller that is configured to receive the measured environment parameters and/or the monitored physiological parameters from the one or more sensors, process them therein, and wirelessly transmit the processed environment parameters and/or the processed physiological parameters to a database and/or a smart electronic device.

8. The bed system of claim 7, wherein the controller is further configured to individually or cooperatively control operations of the adjustable assembly, the plurality of fans, and the aromatherapy system, by operation instruction received from a remote control and/or an APP installed in a smart electronic device.

9. A bed system, comprising:
   a frame structure;
   a plurality of platforms disposed on the frame structure; and
   an adjustable assembly coupled with the frame structure and the plurality of platforms for operably adjusting one or more of the plurality of platforms in desired positions;
   a plurality of fans mounted onto openings in the plurality of platforms and adapted for operably providing air circulation in a surrounding space of the bed system; and
   an aromatherapy system attached onto one or more of the plurality of platforms for producing desired fragrance in the surrounding space so as to promote health and well-being of a user,
   wherein the adjustable assembly comprises:
      a back lifting assembly comprising a back lifting bracket pivotally connected to the frame structure, and a back lifting actuator pivotally connected between the back lifting bracket and the frame structure for operably driving the back lifting bracket to pivotally move in an upward rotating direction or a downward rotating direction relative to the frame structure; and
      a leg lifting assembly comprising a leg lifting bracket pivotally connected to the frame structure, and a leg lifting actuator pivotally connected between the leg lifting bracket and the frame structure for operably driving the leg lifting bracket to pivotally move in an upward rotating direction or a downward rotating direction relative to the frame structure,
   wherein the leg lifting bracket comprises a middle bar and a pair of swing arms, wherein the pair of swing arms is transversely spaced and longitudinally extended, and rigidly connected to ends of the transversely extending middle bar, and each of the pair of swing arms has a first end portion and an opposite, second end portion, wherein the first end portion of each swing arm is pivotally mounted to the frame structure; and
   wherein the leg lifting actuator comprises a motor member, an outer tube extending from the motor member, an activation rod received in the outer tube, engaged with the motor member and configured to be telescopically movable relative to said outer tube according to a direction of motor rotation, wherein the motor member is pivotally connected to the frame structure, and the activation rod has a distal end portion pivotally connected to the middle bar of the leg lifting bracket, or wherein the motor member is pivotally connected to the middle bar of the leg lifting bracket, and the activation rod has a distal end portion pivotally connected to the frame structure.

10. The bed system of claim 9, wherein
   the back lifting bracket comprises a middle bar and a pair of swing arms, wherein the pair of swing arms is transversely spaced and longitudinally extended, and rigidly connected to ends of the transversely extending middle bar, and each of the pair of swing arms has a first end portion and an opposite, second end portion, wherein the first end portion of each swing arm is pivotally mounted to the frame structure; and
   the back lifting actuator comprises a motor member, an outer tube extending from the motor member, an activation rod received in the outer tube, engaged with the motor member and configured to be telescopically movable relative to said outer tube according to a direction of motor rotation, wherein the motor member is pivotally connected to the frame structure, and the activation rod has a distal end portion pivotally connected to the middle bar of the back lifting bracket, or wherein the motor member is pivotally connected to the middle bar of the back lifting bracket, and the activation rod has a distal end portion pivotally connected to the frame structure.

* * * * *